US012570692B2

(12) United States Patent
Li et al.

(10) Patent No.: US 12,570,692 B2
(45) Date of Patent: Mar. 10, 2026

(54) OLIGOPEPTIDE LINKER INTERMEDIATE AND PREPARATION METHOD THEREOF

(71) Applicant: MABPLEX INTERNATIONAL CO., LTD., Shandong (CN)

(72) Inventors: Lele Li, Yantai (CN); Changjiang Huang, Yantai (CN)

(73) Assignee: MABPLEX INTERNATIONAL CO., LTD., Shandong (CN)

( * ) Notice: Subject to any disclaimer, the term of this patent is extended or adjusted under 35 U.S.C. 154(b) by 0 days.

(21) Appl. No.: 17/978,800

(22) Filed: Nov. 1, 2022

(65) Prior Publication Data

US 2023/0128167 A1 Apr. 27, 2023

Related U.S. Application Data

(62) Division of application No. 16/630,080, filed as application No. PCT/CN2019/112671 on Oct. 23, 2019, now abandoned.

(51) Int. Cl.

| | |
|---|---|
| ***C07K 5/06*** | (2006.01) |
| ***A61K 47/65*** | (2017.01) |
| ***C07K 1/06*** | (2006.01) |
| ***C07K 5/062*** | (2006.01) |
| ***C07K 5/08*** | (2006.01) |
| ***C07K 5/10*** | (2006.01) |

(52) U.S. Cl.

CPC .......... *C07K 5/06052* (2013.01); *A61K 47/65* (2017.08); *C07K 1/063* (2013.01); *C07K 5/06191* (2013.01); *C07K 5/0827* (2013.01); *C07K 5/1027* (2013.01)

(58) Field of Classification Search

CPC .............. C07K 5/06191; C07K 5/1027; C07K 5/0827; C07K 1/063; A61K 47/65; A61K 47/6803

See application file for complete search history.

(56) References Cited

FOREIGN PATENT DOCUMENTS

| | | |
|---|---|---|
| CN | 108025084 | 5/2018 |
| RU | 2018102153 | 7/2019 |
| WO | WO 2019/108797 | 6/2019 |

OTHER PUBLICATIONS

Dal Corso et al., "Protease-cleavable linkers modulate the anticancer activity of non-internalizing antibody-drug conjugates," *Bioconjugate Chemistry*, 28(7):1826-1833, 2017.

English translation of the International Search Report and Written Opinion issued in International Patent Application No. PCT/CN2019/112671, dated Jul. 16, 2020.

English translation of Office Action issued in Russian Patent Application No. 2021105635, dated Aug. 25, 2021.

Extended European Search Report issued in European Patent Application No. 19820986.8, dated Oct. 1, 2021.

Gao et al., "Total synthesis of the putative structure of the proposed Banyasin A," *Frontiers in Chemistry*, 3(19):7 pages, 2015.

Gille and Kirschning, "Studies on the synthesis of peptides containing dehydrovaline and dehydroisoleucine based on copper-mediated enamide formation," *Beilstein J. Org. Chem.*, 12:564-570, 2016.

Li, Zhaohui, "Preparation and Preliminary Study on Biological Activities of Several Anti-CD20 Antibody Drug Conjugates," Chinese Doctoral Dissertations Full-Text Database, *Medical and Health Sciences*, 12 (2013): 1-149.

Lipshutz, B. H. et al., "Triisopropylsilyloxycarbonyl ("Tsoc"): A New Protecting Group for 1° and 2° Amines," *J. Org. Chem.*, 64 (1999): 3792-3793.

Mondal, D. et al., "Improved Methodology for the Synthesis of a Cathepsin B Cleavable Dipeptide Linker, Widely Used in Antibody-Drug Conjugate Research," *Tetrahedron Letters*, 59(40):3594-3599, 2018.

Office Communication issued in Australian Patent Application No. 2019284038, dated Sep. 30, 2020.

Okada et al., "Chemical synthesis of ComX pheromone and related peptides containing isoprenoidal tryptophan residues," *Tetrahedron*, 62:8907-8918, 2006.

Okada et al., "Structure of the Bacillus subtilis quorum-sensing peptide pheromone ComX," *Nature Chemical Biology*, (1):23-4, 2005.

Shute and Rich, "Synthesis and Evaluation of Novel Activated Mixed Carbonate Reagents for the Introduction of the 2-(Trimethylsilyl)ethoxycarbonyl(Teoc)-Protecting Group," 1987(4):346-349, 1987.

Supporting Information for Dal Corso et al., "Protease-cleavable linkers modulate the anticancer activity of non-internalizing antibody-drug conjugates," *Bioconjugate Chemistry*, 28(7):1826-1833, pp. S1-S24, 2017.

Wuensch, E. et al., "Synthesis of 2-(trimethylsilyl)ethyloxycarbonylamino acids and their use in peptide chemistry," *Hoppe-Seyler's Zeitschrift fuer Physiologische Chemie*, 362.9 (1981): 1289-1292.

Wuts et al., "Protection for the amino group," In: Greene's Protective Groups in Organic Synthesis, John Wiley & Sons, Inc., Chapter 7, pp. 719-722, 2007.

Zhou, Liang et al., "Synthesis of End N-Teoc Protected Amino Acid," *Zhejang Chenmical Industry*, 46.5 (2015): 1-3.

*Primary Examiner* — Sudhakar Katakam

(74) *Attorney, Agent, or Firm* — pH IP Law

(57) ABSTRACT

The invention provides a new oligopeptide linker intermediate and a preparation method thereof. The preparation method of the oligopeptide intermediate is easily carried out under mild reaction conditions, and since almost no side reactions occur in the reaction, the method produces a high-purity product with fewer impurities and easy to be purified, achieving unexpected technical effects.

2 Claims, 8 Drawing Sheets

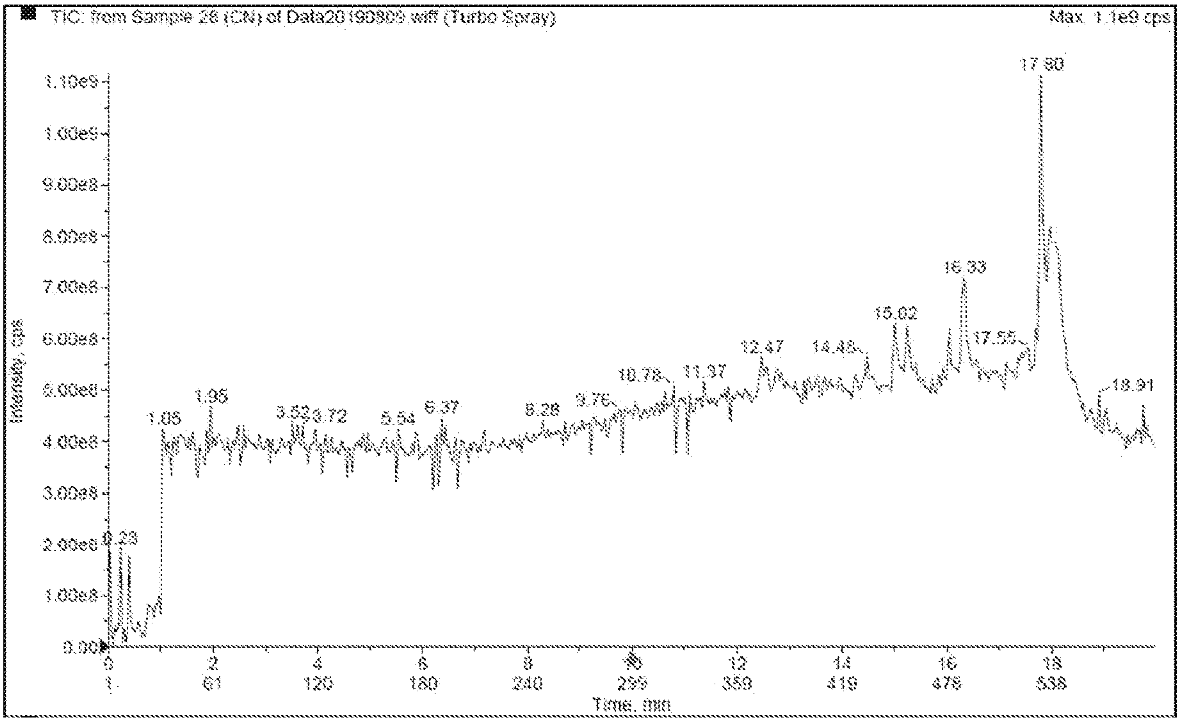
Figure 1-A
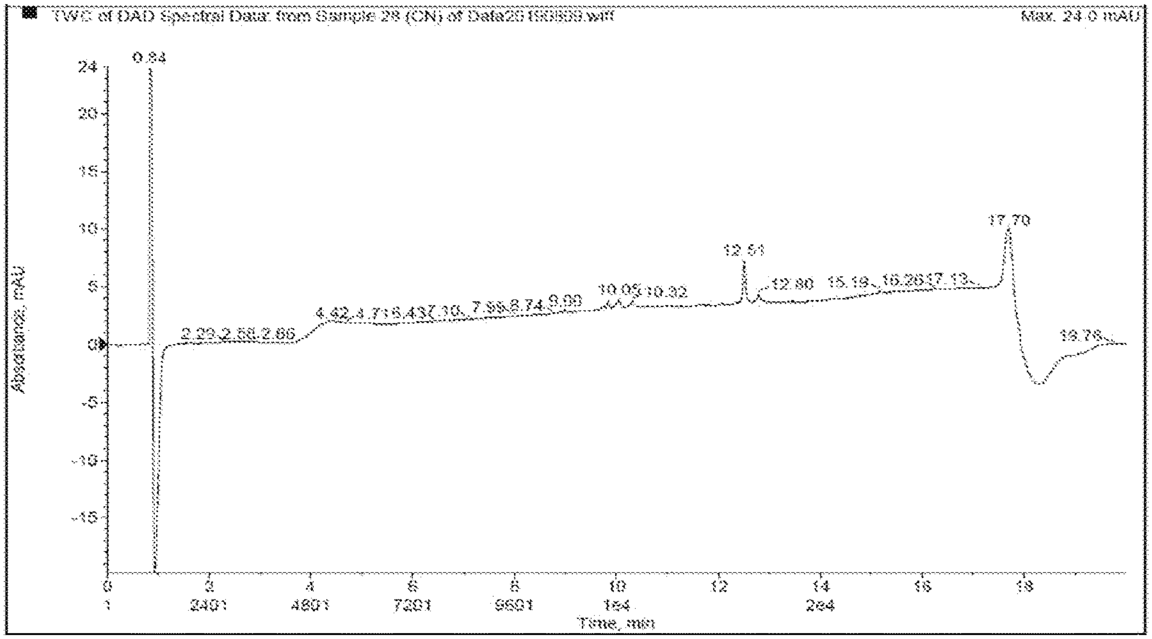
Figure1-B

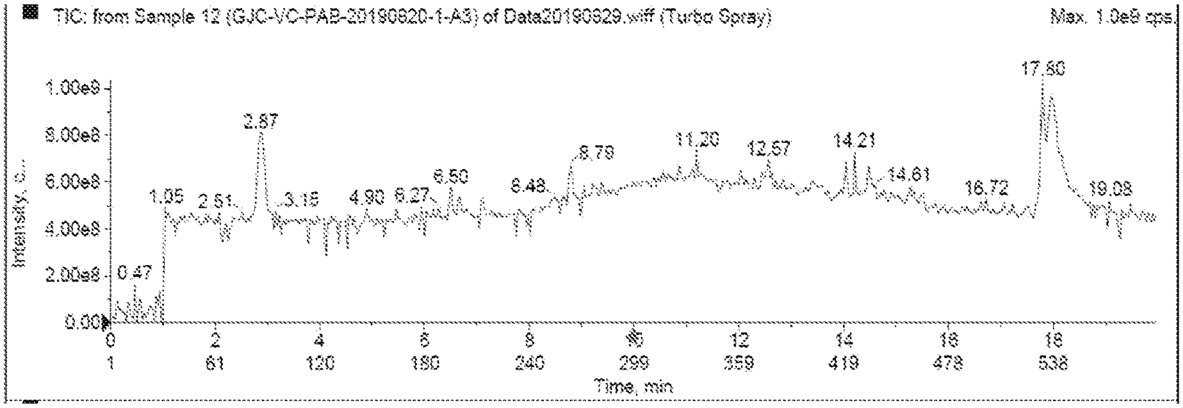
Figure 1-C
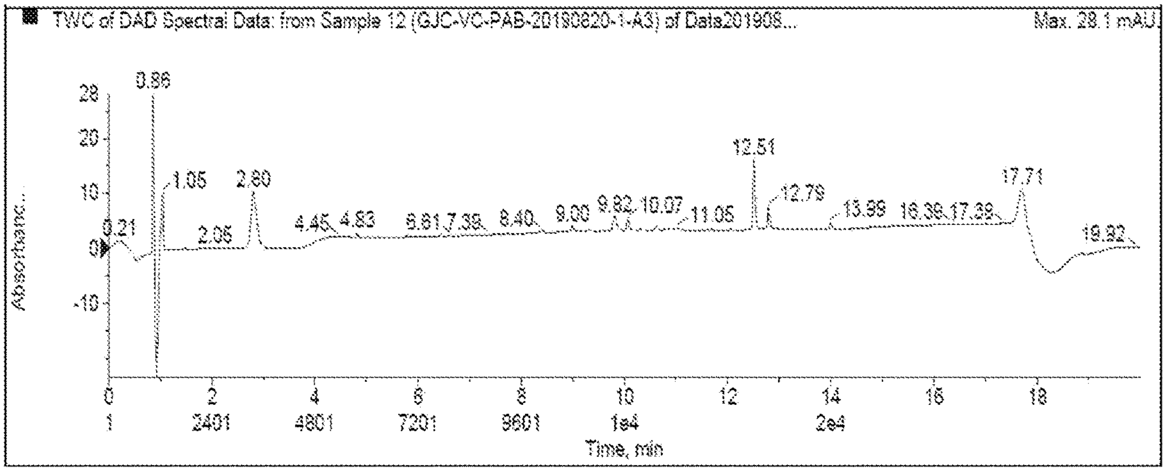
Figure 1-D
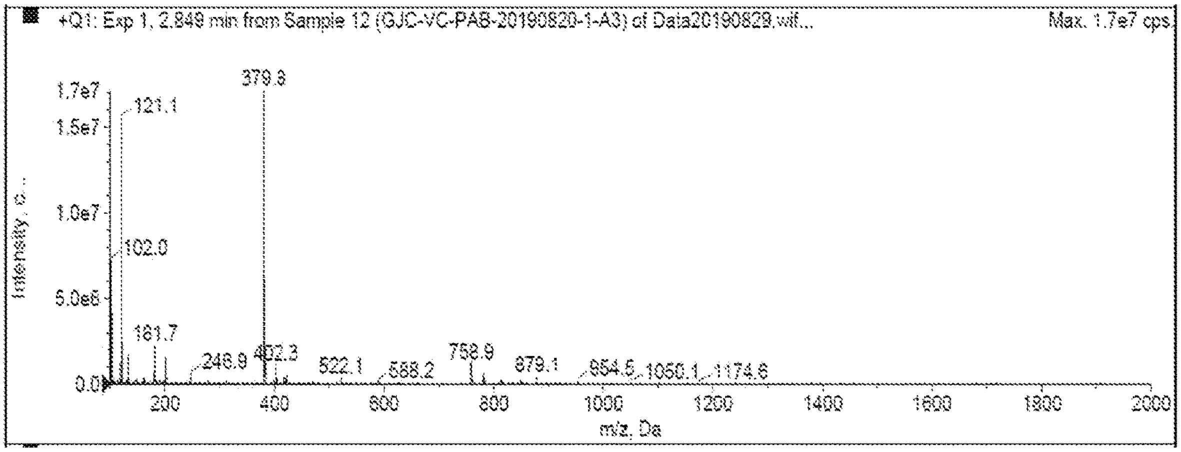
Figure 1-E

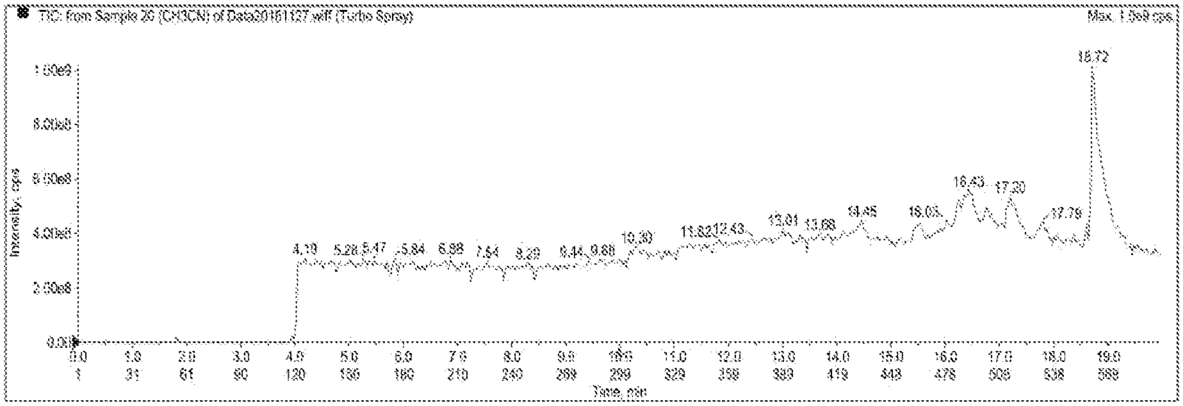
Figure 1-F
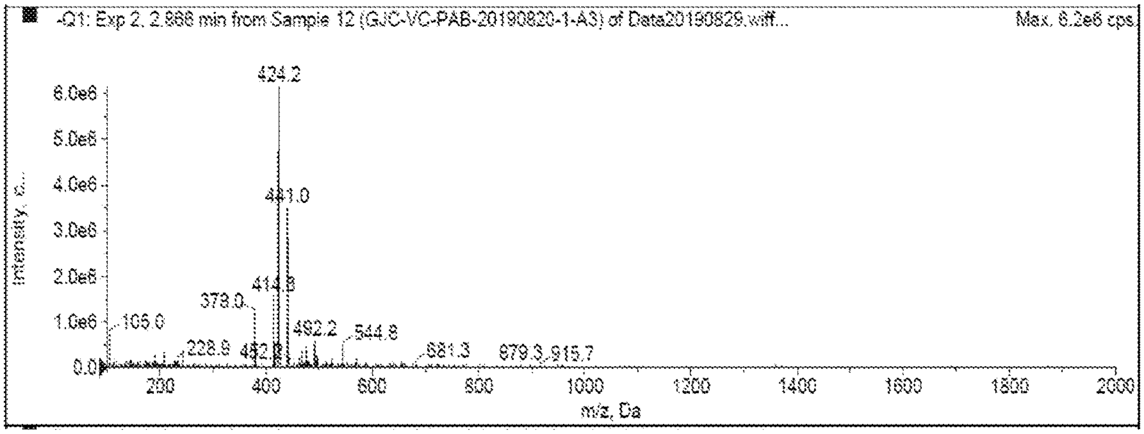
Figure 2-A

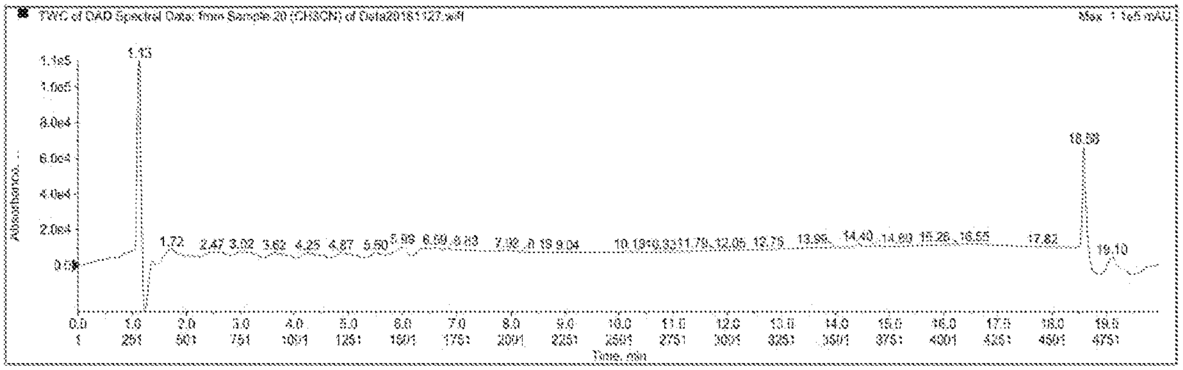
Figure 2-B
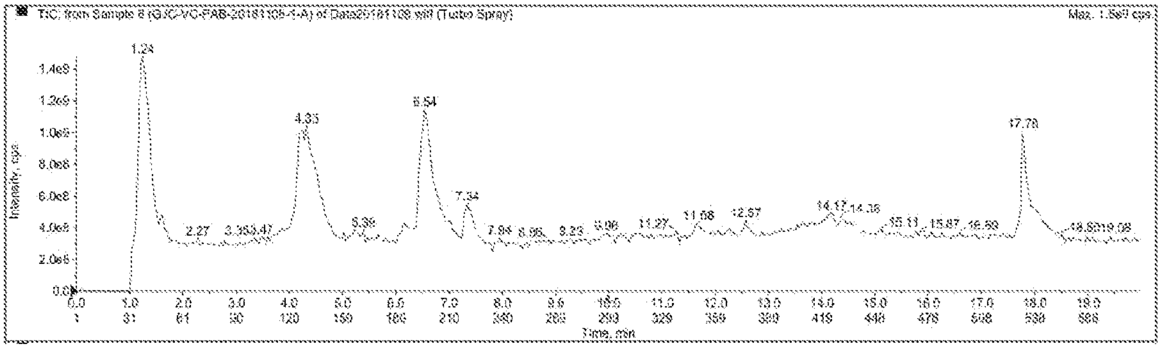
Figure 2-C
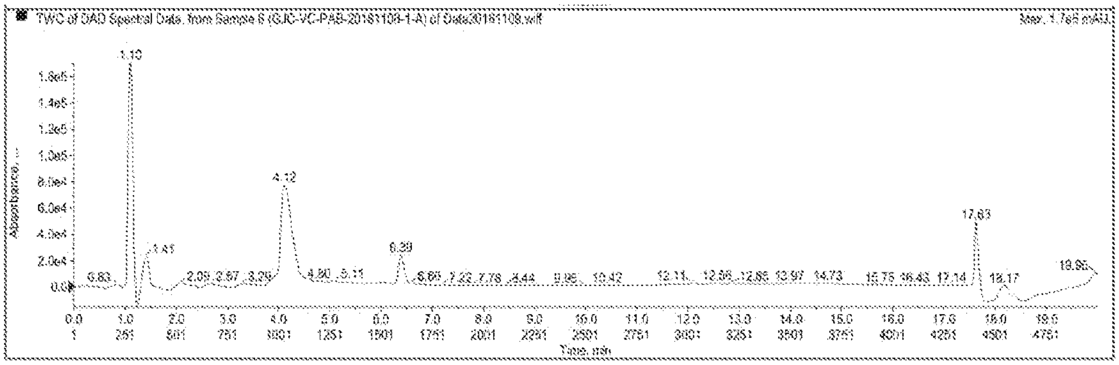
Figure 2-D

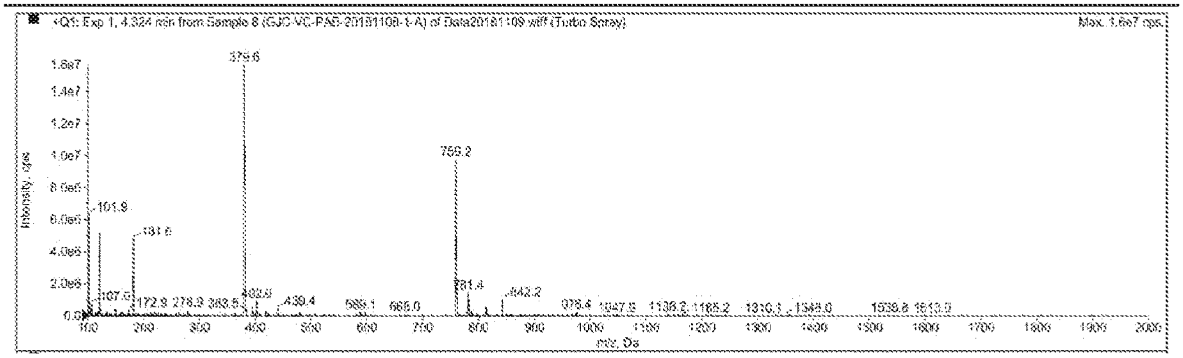
Figure 2-E
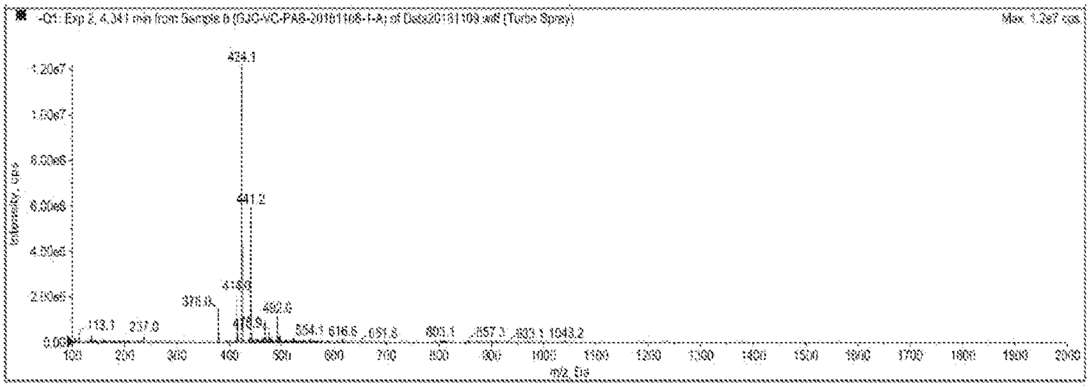
Figure 2-F
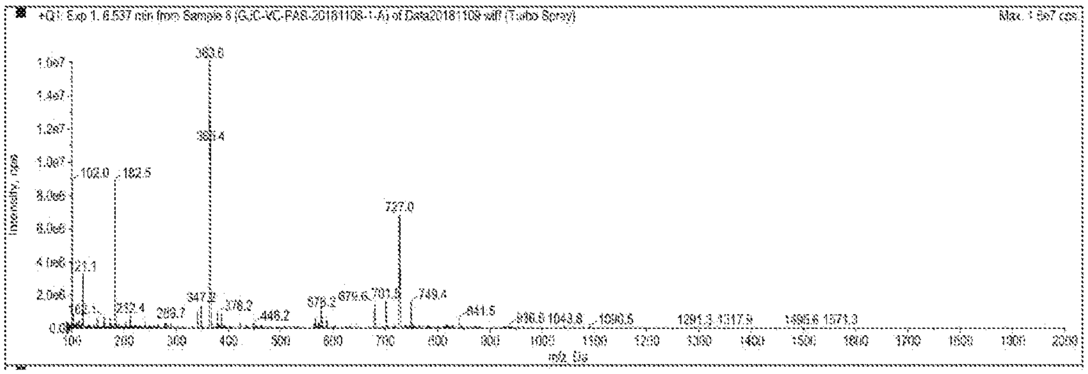
Figure 2-G

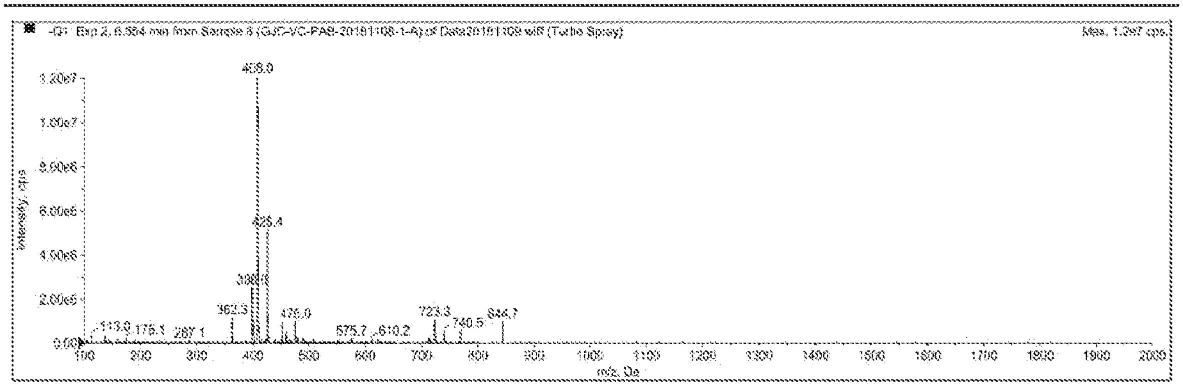
Figure 2-H
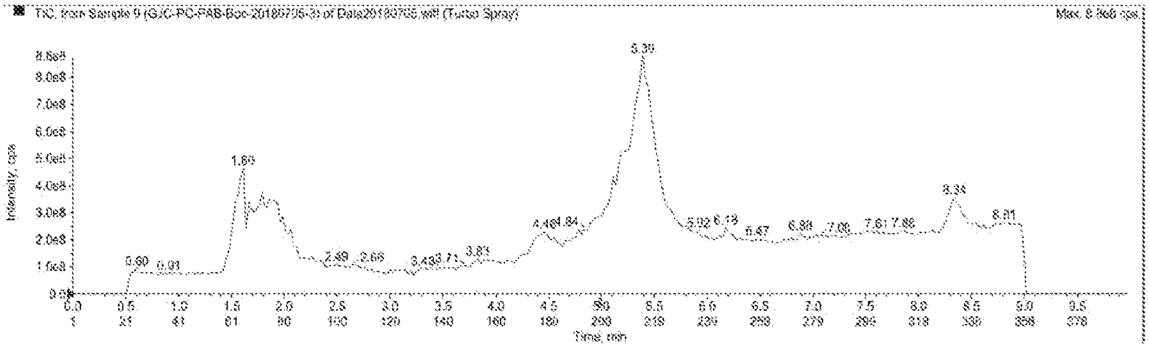
Figure 3-A
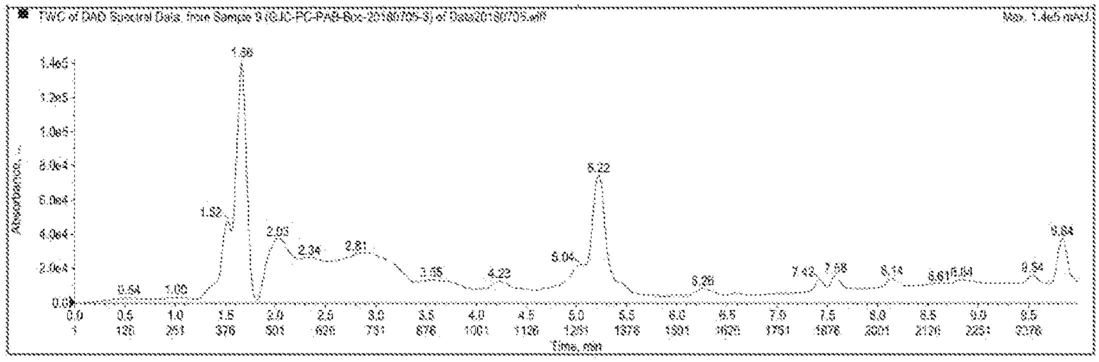
Figure 3-B

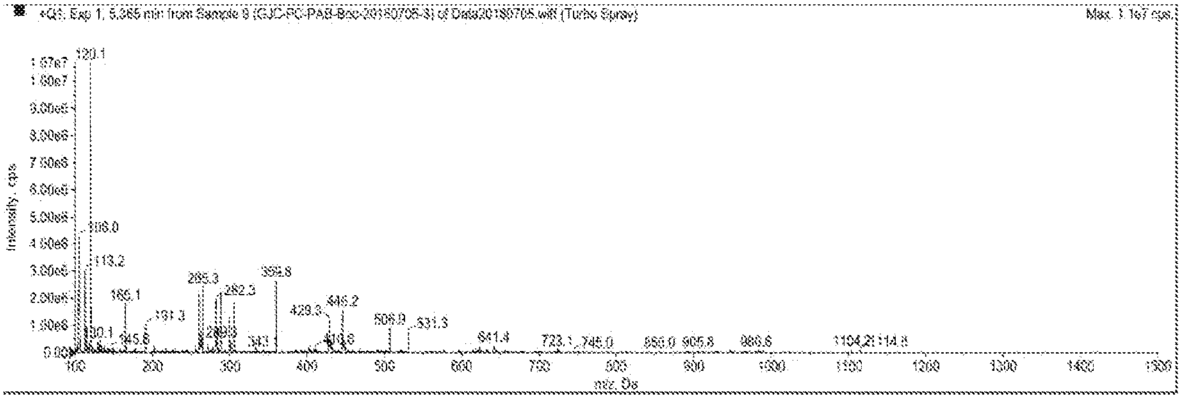
Figure 3-C
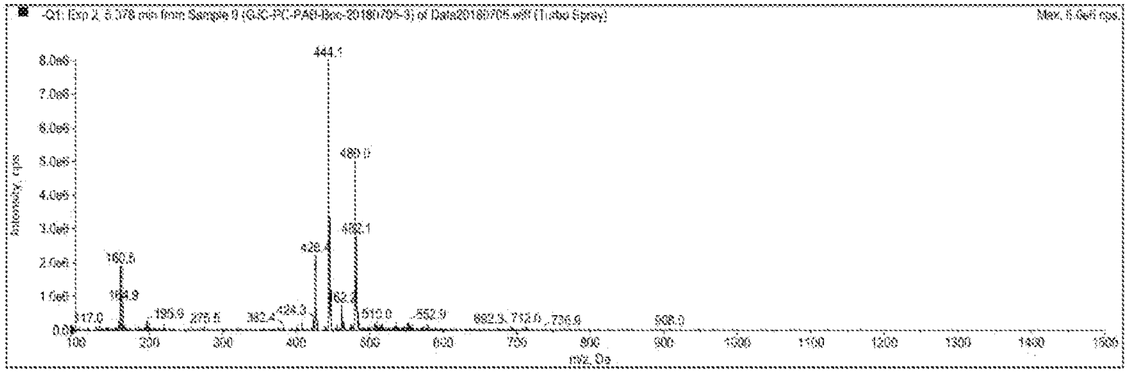
Figure 3-D
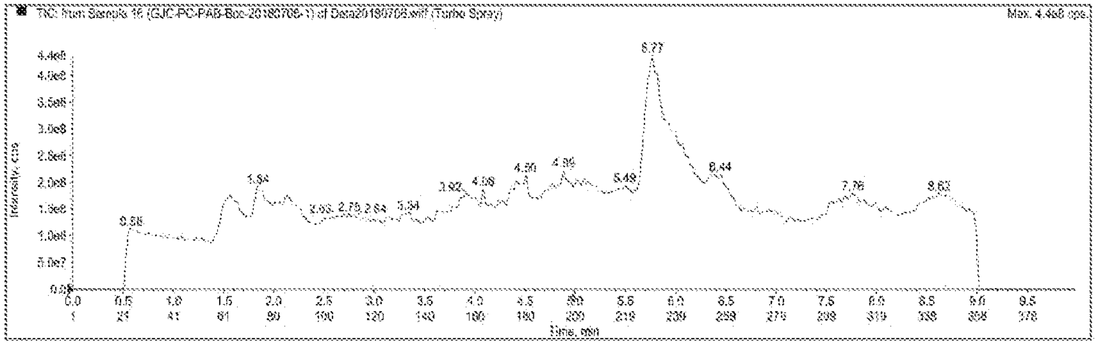
Figure 4-A

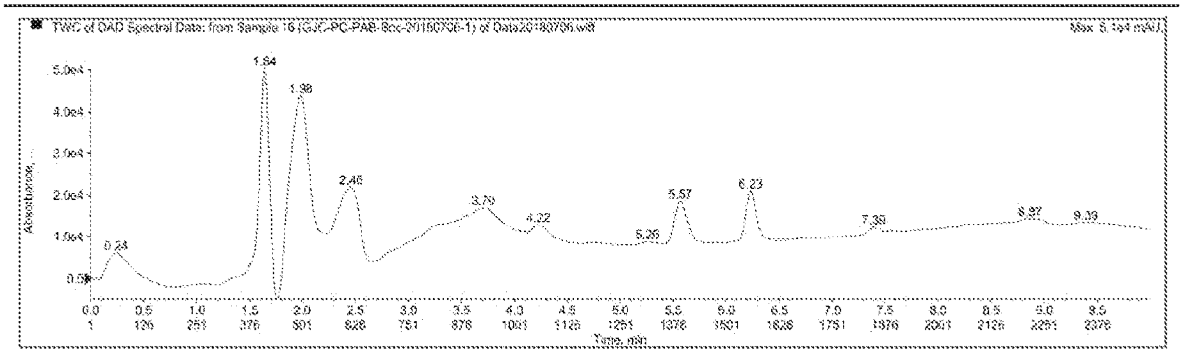
Figure 4-B
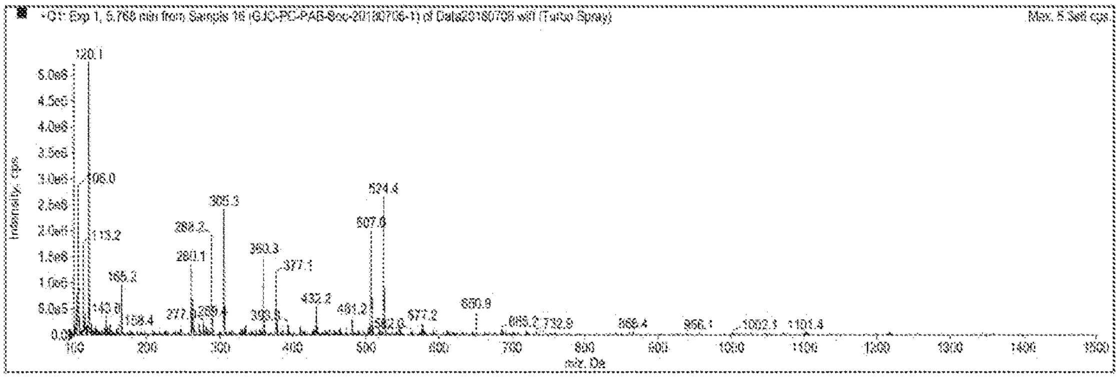
Figure 4-C
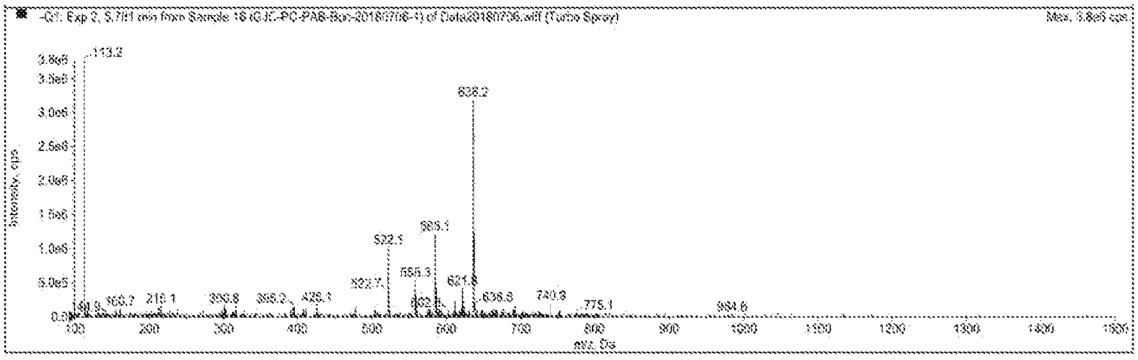
Figure 4-D

OLIGOPEPTIDE LINKER INTERMEDIATE AND PREPARATION METHOD THEREOF

This application is a divisional of U.S. application Ser. No. 16/630,080, filed Jan. 10, 2020, which is a national phase application under 35 U.S.C. § 371 of International Application No. PCT/CN2019/112671, filed Oct. 23, 2019, the entirety of each of which is incorporated herein by reference.

FIELD OF THE INVENTION

The present invention relates to the field of antibody-drug conjugates, and in particular, to a method for preparing an oligopeptide linker and an intermediate thereof.

BACKGROUND OF THE INVENTION

Antibody-Drug Conjugate (ADC), as a new type of biological missile, achieves an advantageous combination of the targeting effect of monoclonal antibodies and the cytotoxicity effect of small molecule drugs, and has now become one of the fastest developing fields in tumor targeting therapy. The three components (an antibody, a cytotoxin and a linker) of an ADC constitute a targeted drug delivery system, in which the construction and optimization of linkers are crucial for the development of such system. Linkers are the basis for the effective delivery of cytotoxic drugs through ADCs, and the key factor in determining the toxicity of ADC products, because the premature release of drugs into the blood circulation may lead to systemic toxicity and a lower therapeutic index. By optimizing the existing coupling technology, developing stable linkers, and exploring new toxin release mechanisms, it is possible to solve the problems such as off target action of toxins and drug resistance commonly observed in ADC, thereby further improving the efficacy and safety.

At the present stage, oligopeptide-based cleavable ADCs which are degraded under the action of cathepsin B in the lysosomes of target cells to release toxins to ultimately kill tumors are the main focus (Reference 1: Wang Y, S, Zhong W, et al. Development and properties of valine-alanine based antibody-drug conjugates with monomethyl auristatin e as the potent payload[J]. International journal of molecular sciences, 2017, 18(9): 1860). Among them, oligopeptide linkers (such as valine-citrulline dipeptide (Val-Cit, VC)) have been widely used in various ADC drugs. In the five antibody-conjugated drugs currently approved (as of July 2019) (Table 1), the linkers of Brentuximab vedotin of Seattle & Takeda and Polatuzumab vedotin-piiq of Genentech are oligopeptide linkers (valine-citrulline dipeptide linker),

TABLE 1

Commercially available antibody drug conjugates

| Generic name | Company | Time to market | Target | Linker | Drug moiety |
|---|---|---|---|---|---|
| Brentuximab vedotin | Seattle, Takeda | 2011 | CD30 | Mc-Val-Cit-PAB | MMAE |
| Trastuzumab emtansine | Genentech | 2013 | Her2 | MCC (thioether linker) | DM1 |
| Inotuzumab ozogamicin | Pfizer | 2017 | CD22 | 4-(4-acetylphenoxy) butanoic acid | Ozogamicin |
| Gemtuzumab ozogamicin | Pfizer | 2017 | CD33 | 4-(4-acetylphenoxy) butanoic acid | Ozogamicin |
| Polatuzumab vedotin-piiq | Genentech | 2019 | CD79b | Mc-Val-Cit-PAB | MMAE |

There are currently three main methods for synthesizing oligopeptide linkers (Reference 2: Mondal D, Ford J, Pinney K G. Improved Methodology for the Synthesis of a Cathepsin B Cleavable Dipeptide Linker, Widely Used in Antibody-Drug Conjugate Research [J]. Tetrahedron letters, 2018, 59 (40): 3594-3599), in which the first method uses Fmoc protecting group, the second uses Cbz protecting group, and the third uses Boc protecting group.

The above three preparation processes are described below using valine-citrulline dipeptide linkers as examples:

(1) Using Fmoc Protecting Group

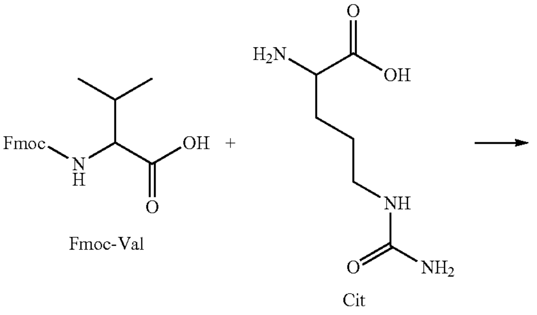

Fmoc-Val

Cit

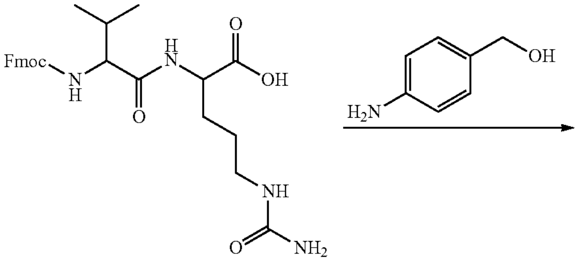

Fmoc-Val-Cit

-continued

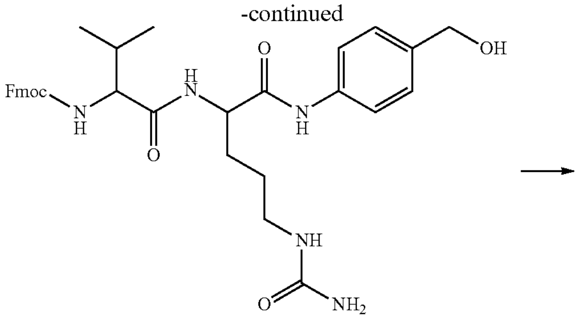

Fmoc-Val-Cit-PAB

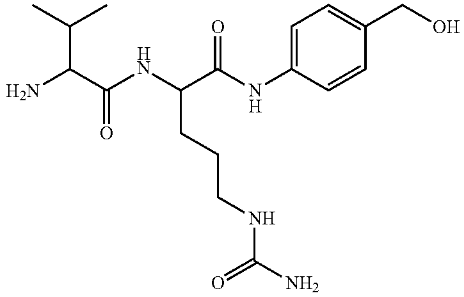

Val-Cit-PAB

In this method, Fmoc-Val is first condensed with Cit to obtain Fmoc-Val-Cit, which then is condensed with p-aminobenzyl alcohol to obtain Fmoc-Val-Cit-PAB, and then Fmoc is removed to give Val-Cit-PAB. However, lower amines are usually used in this method to remove the Fmoc protecting group, so that byproducts are easily formed and hard to completely remove. In addition, Fmoc has strong UV absorption, and trace residues have a great impact on the purity test of the product.

(2) Using Cbz Protecting Group

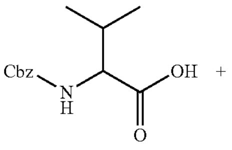

Cbz-Val

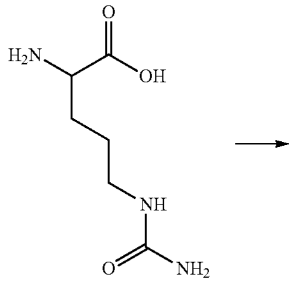

Cit

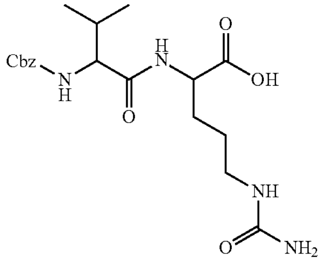

Cbz-Val-Cit

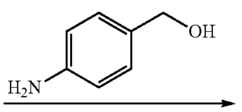

-continued

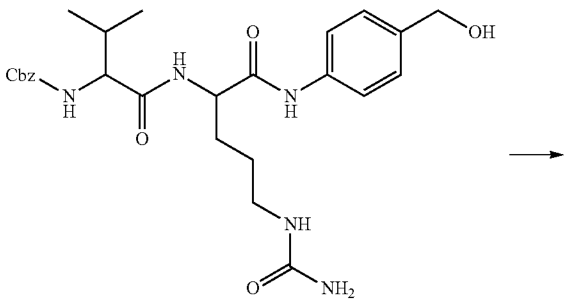

Cbz-Val-Cit-PAB

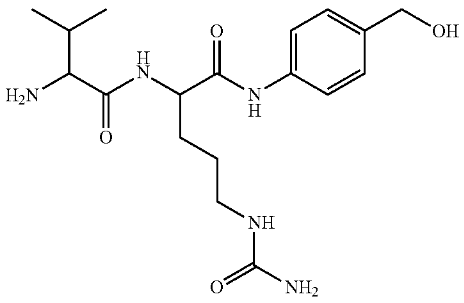

Val-Cit-PAB

In this method, Cbz-Val is first condensed with Cit to obtain Cbz-Val-Cit, which then is condensed with p-aminobenzyl alcohol to obtain Cbz-Val-Cit-PAB, and then Val-Cit-PAB is obtained by removing Cbz. However, transition metal, usually Pd, is required as the catalyst when removing the Cbz protecting group in this method, which is harmful to the human body by resulting in heavy metal residues which is hard to remove. In addition, a hydrogen source is required, usually hydrogen gas, which is extremely explosive, leading to high safety risks and unsuitable for large-scale use. Although other hydrogen sources may be used, some hydrogen gas is also released during use, bringing safety risks.

(3) Using Boc Protecting Group

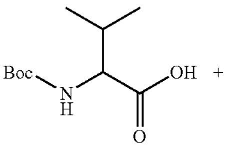

Boc-Val

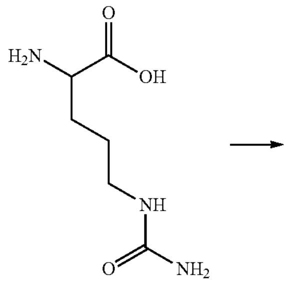

Cit

-continued

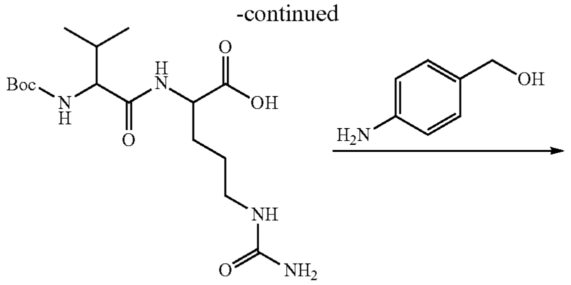

Boc-Val-Cit

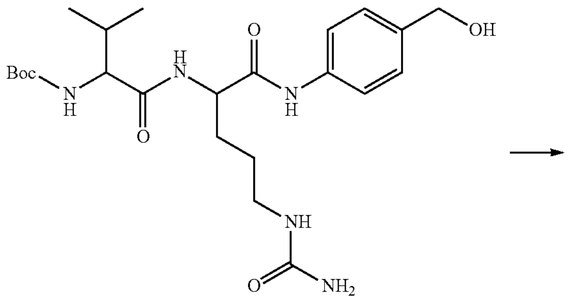

Boc-Val-Cit-PAB

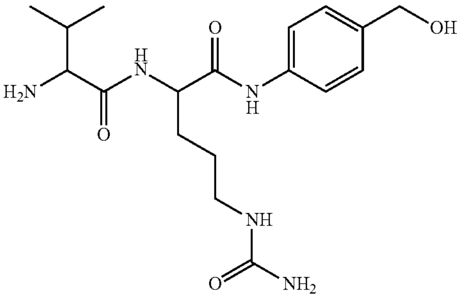

Val-Cit-PAB

In this method, Boc-Val is first condensed with Cit to obtain Boc-Val-Cit, which then is condensed with p-aminobenzyl alcohol to obtain Boc-Val-Cit-PAB, and then Val-Cit-PAB is obtained by removing Boc. This method uses strong acid, usually HCl solution and trifluoroacetic acid, to remove the Boc protecting group. When using HCl, the alcoholic hydroxyl at the benzyl position of the Boc-Val-Cit-PAB molecule will be replaced by chlorine to form the corresponding benzyl chloride, which would affects product quality. When using trifluoroacetic acid, the alcohol at the benzyl position will undergo an esterification reaction to give the corresponding trifluoroacetate, therefore an additional step of hydrolysis reaction is required to obtain Val-Cit-PAB. In addition, the basic hydrolysis has the risk of racemizing the chiral center of the amino acid units.

SUMMARY OF THE INVENTION

In order to solve the above problems, the present invention provides a new method for preparing oligopeptide linkers. The method for preparing Val-Cit-PAB using Teoc as the protecting group provided by the present invention is easily carried out under mild reaction conditions, and since almost no side reactions occur in the reaction, the method produces a high-purity product with fewer impurities and easy to be purified, achieving unexpected technical effects.

Specifically, the present invention provides an oligopeptide linker intermediate, with the structure as shown in formulas (1)-(4):

(1)

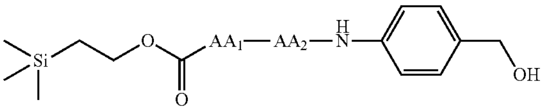

or (2)

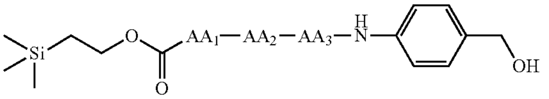

or (3)

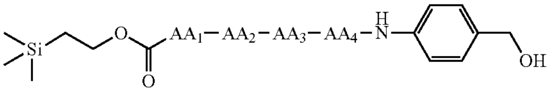

or (4)

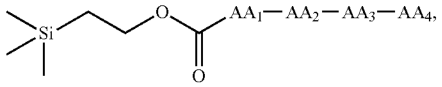

wherein, the $AA_1$, $AA_2$, $AA_3$ and AA4 are any amino acid.

Further, the $AA_1$, $AA_2$, $AA_3$, and $AA_4$ are independently selected from the group consisting of -valine- (-Val-), -citrulline -(-Cit-), -alanine- (-Ala-), -lysine- (-Lys-), -lysine (trityl)- (-Lys(Trt)-), -lysine(monomethoxytrityl)- (-Lys (Mmt)-), -lysine(fluorenylmethyloxycarbonyl)- (-Lys (Fmoc)-), -arginine- (-Arg-), -phenylalanine- (-Phe-), -glycine- (-Gly-), -leucine- (-Leu-), and -isoleucine- (-Ile-).

Furthermore, the $-AA_1-AA_2-$ is selected from the group consisting of -valine- citrulline- (-Val-Cit-), -valine-alanine- (-Val-Ala-), -valine-lysine- (-Val-Lys-), -valine- lysine(trityl)- (-Val-Lys(Trt)-), -valine-lysine(monomethoxytrityl)- (-Val-Lys(Mmt)-), -valine-lysine(fluorenylmethyloxycarbonyl)- (Val-Lys(Fmoc)-), -valine-arginine- (-Val-Arg-), -phenylalanine-citrulline- (-Phe-Cit-), -phenylpropyl-lysine- (-Phe-Lys-), -phenylalanine-lysine(trityl)- (-Phe-Lys(Trt)-), -phenylalanine-lysine(monomethoxytrityl)- (-Phe-Lys (Mmt)-), -phenylalanine-lysine (fluorenylmethyloxycarbonyl)- (-Phe-Lys(Fmoc)-), leucine-citrulline- (-Leu-Cit-), isoleucine-citrulline- (-Ile-Cit-) and -phenylalanine-arginine- (-Phe-Arg-); the $-AA_1-AA_2-AA_3-$ is selected from -phenylalanine-arginine-arginine-(-Ala-Arg-Arg-); the $-AA_1-AA_2-AA_3-AA_4-$ is selected from the group consisting of -glycine-glycine-phenylalanine-glycine- (-Gly-Gly-Phe-Gly-), -glycine-phenylalanine-leucine-glycine- (-Gly-Phe-Leu-Gly-), and -alanine-leucine-alanine-leucine (-Ala-Leu-Ala-Leu-).

Preferably, the oligopeptide linker intermediate includes the following structure:

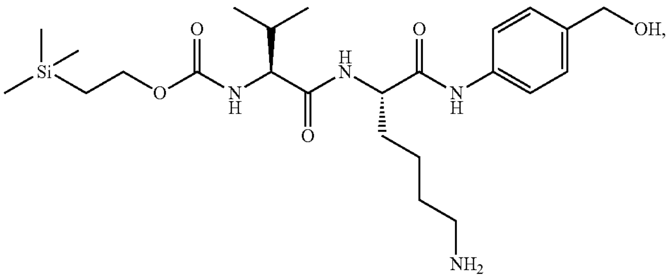
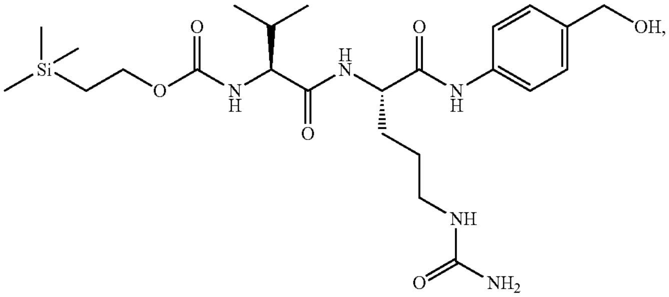
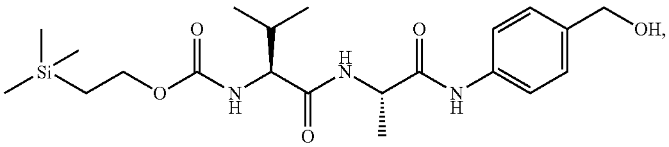
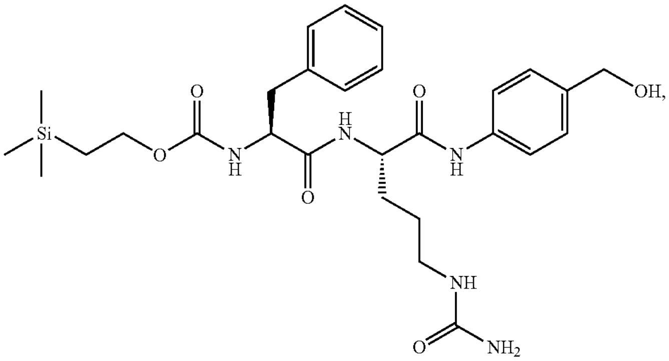
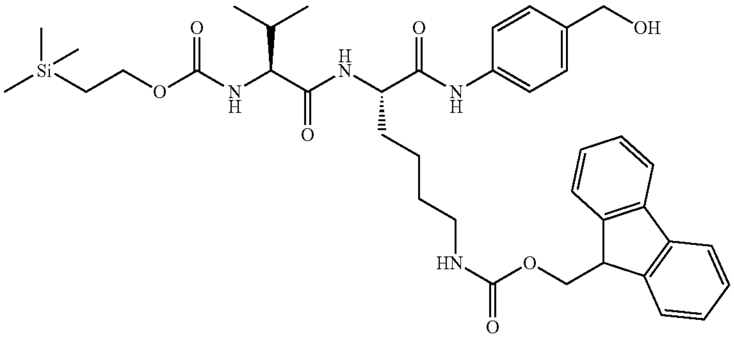
,

-continued
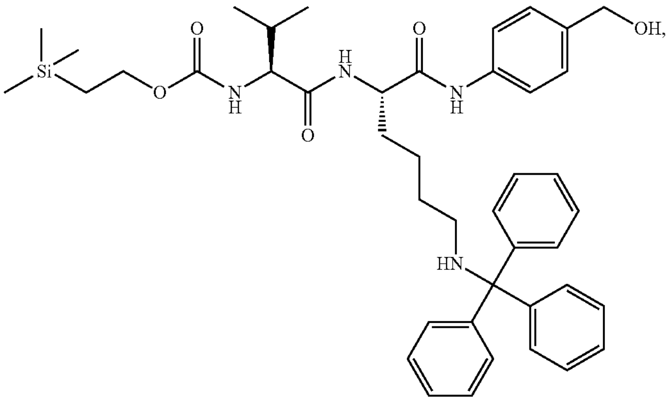
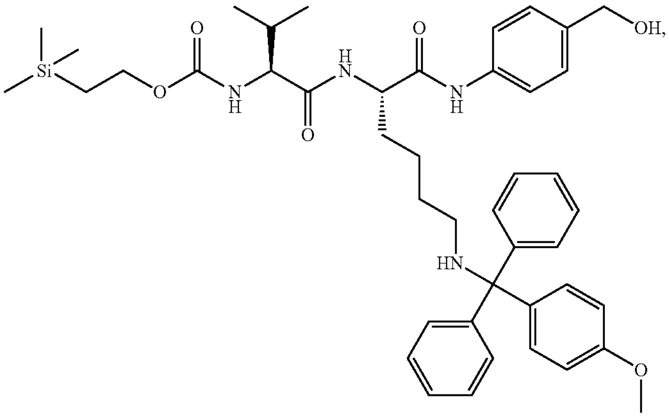
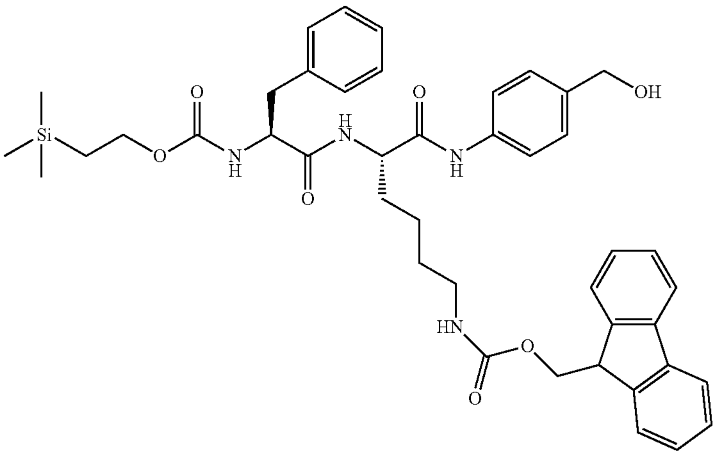
,

-continued
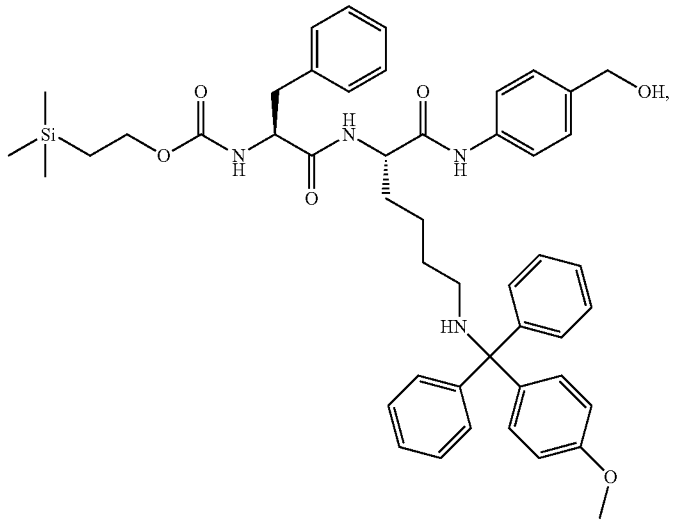
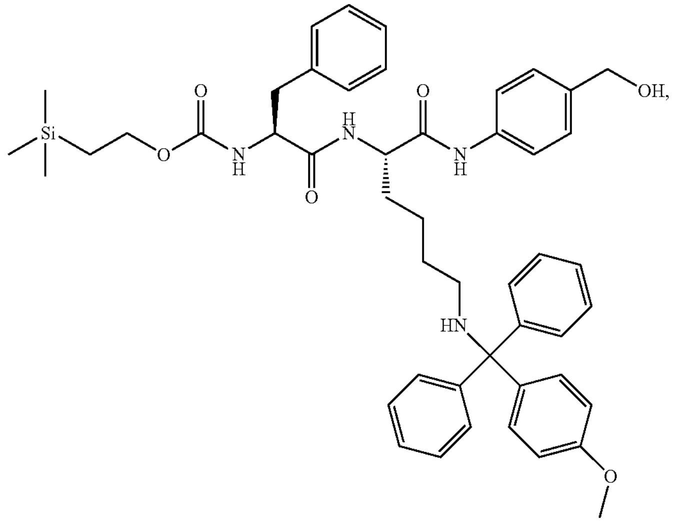
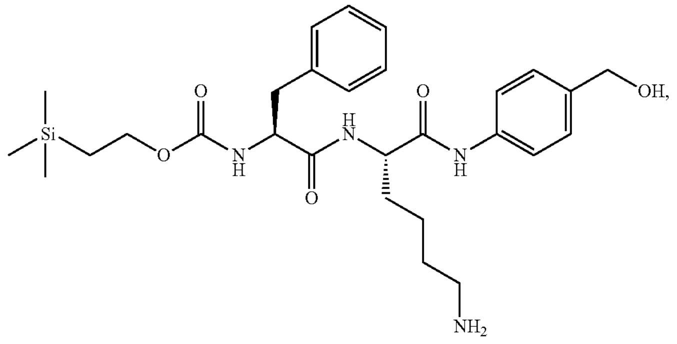

-continued
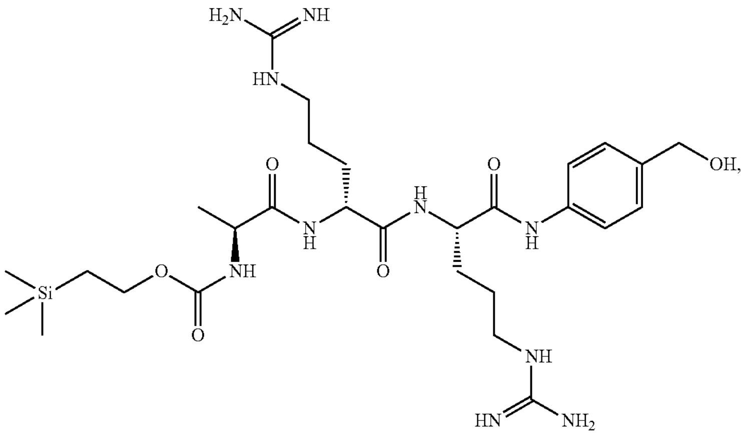
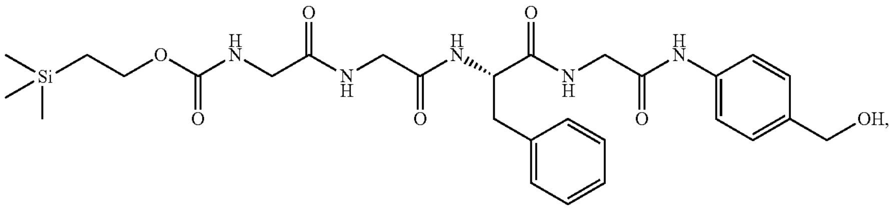
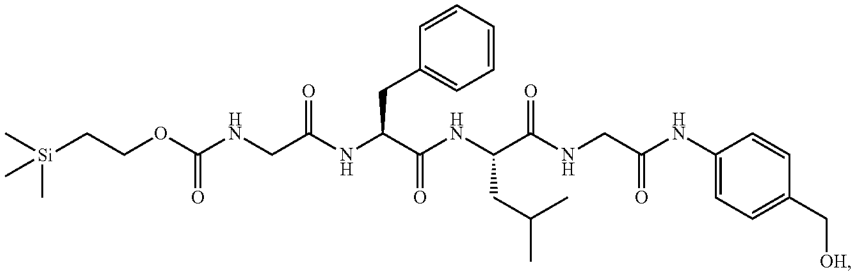
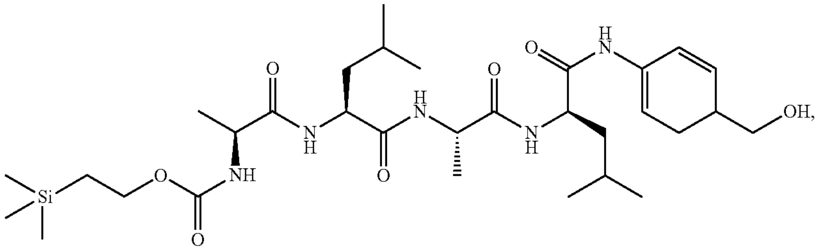
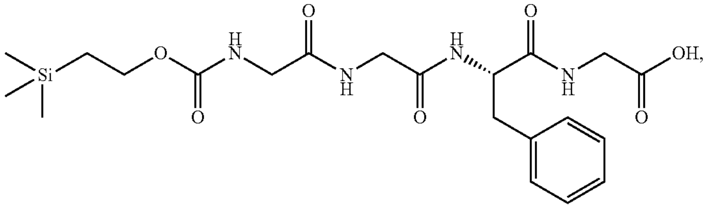
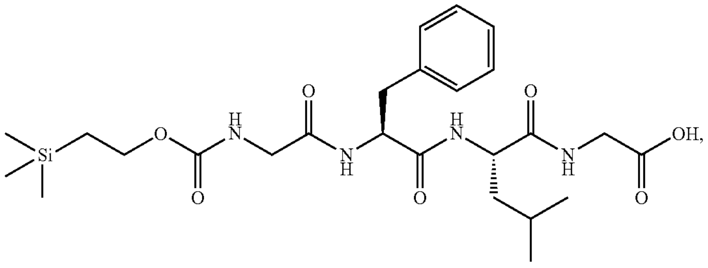

-continued

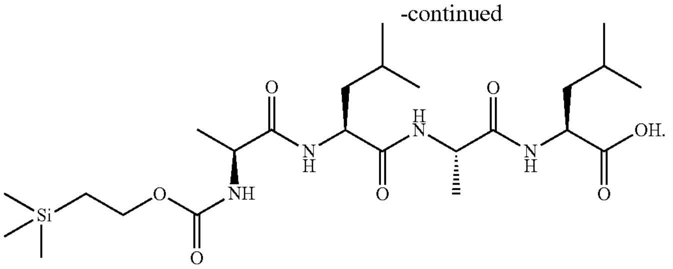

The present invention also provides a method for preparing the oligopeptide linker intermediate of formulae (1) to (3), wherein the reaction route of the method is as follows:

1) performing a condensation reaction between a carbonylation reagent, 2-(trimethylsilyl)ethanol and amino acid $AA_1$, and then amino acid $AA_2$, or amino acid $AA_1$, amino acid $AA_2$ and amino acid $AA_3$ in sequence, or amino acid $AA_1$, amino acid $AA_2$, amino acid $AA_3$ and amino acid $AA_4$ in sequence, to obtain a 2-(trimethylsilyl)ethoxycarbonyl-oligopeptide condensate;
2) reacting the resulting 2-(trimethylsilyl)ethoxycarbonyl-oligopeptide condensate and p-aminobenzyl alcohol to obtain a 2-(trimethylsilyl)ethoxycarbonyl-oligopeptide-p-aminobenzyl alcohol condensate, wherein the carbonylation reagent is any compound containing a carbonyl group.

Further, the oligopeptide linker intermediate of formula (1) is obtained via the following reaction route:

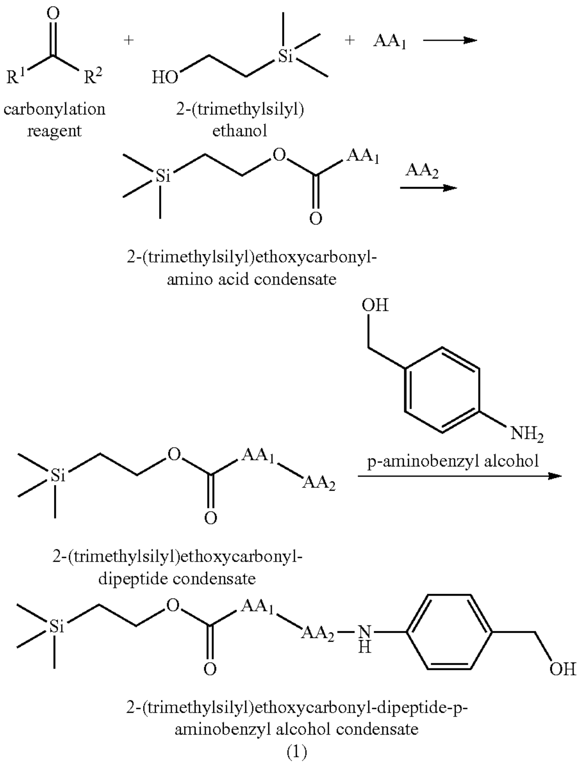

(1)

wherein the preparation method comprises the following steps:

1) performing a condensation reaction between a carbonylation reagent, 2-(trimethylsilyl)ethanol and amino acid $AA_1$ to obtain a 2-(trimethylsilyl)ethoxycarbonyl-amino acid condensate;
2) performing a condensation reaction between the 2-(trimethylsilyl)ethoxycarbonyl-amino acid condensate and amino acid $AA_2$ to obtain a 2-(trimethylsilyl)ethoxycarbonyl-dipeptide condensate; and
3) performing a condensation reaction between the 2-(trimethylsilyl)ethoxycarbonyl-dipeptide condensate and p-aminobenzyl alcohol to obtain a 2-(trimethylsilyl)ethoxycarbonyl-dipeptide-p-aminobenzyl alcohol condensate.

Further, the oligopeptide linker intermediate of formula (2) is obtained via the following reaction route:

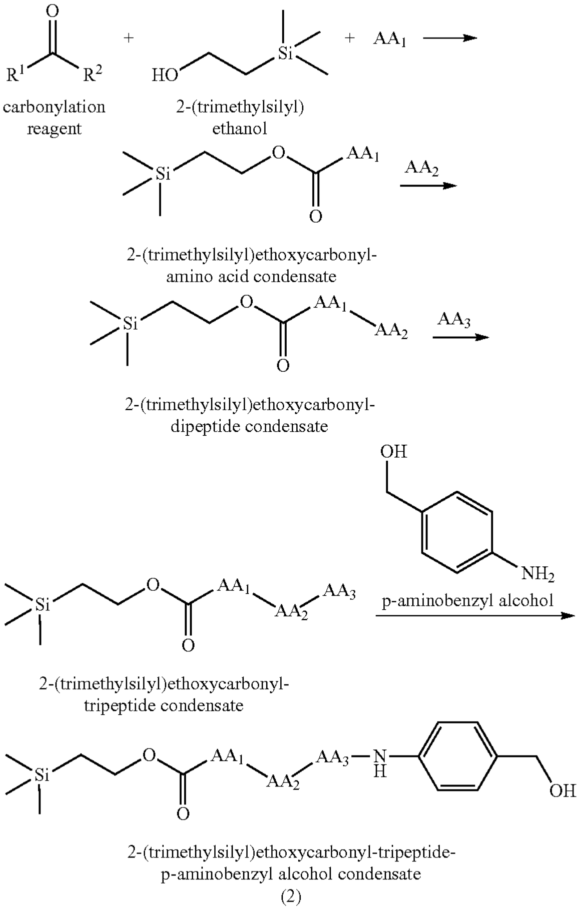

(2)

wherein the preparation method comprises the following steps:

1) performing a condensation reaction between a carbonylation reagent, 2-(trimethylsilyl)ethanol and amino acid $AA_1$ to obtain a 2-(trimethylsilyl)ethoxycarbonyl-amino acid condensate;
2) performing a condensation reaction between the 2-(trimethylsilyl)ethoxycarbonyl-amino acid condensate and amino acid $AA_2$ to obtain a 2-(trimethylsilyl)ethoxycarbonyl-dipeptide condensate;
3) performing a condensation reaction between the 2-(trimethylsilyl)ethoxycarbonyl-dipeptide condensate and amino acid $AA_3$ to obtain a 2-(trimethylsilyl)ethoxycarbonyl-tripeptide condensate; and
4) performing a condensation reaction between the 2-(trimethylsilyl)ethoxycarbonyl-tripeptide condensate and p-aminobenzyl alcohol to obtain a 2-(trimethylsilyl)ethoxycarbonyl-tripeptide-p-aminobenzyl alcohol condensate.

Further, the oligopeptide linker intermediate of formula (3) is obtained via the following reaction route:

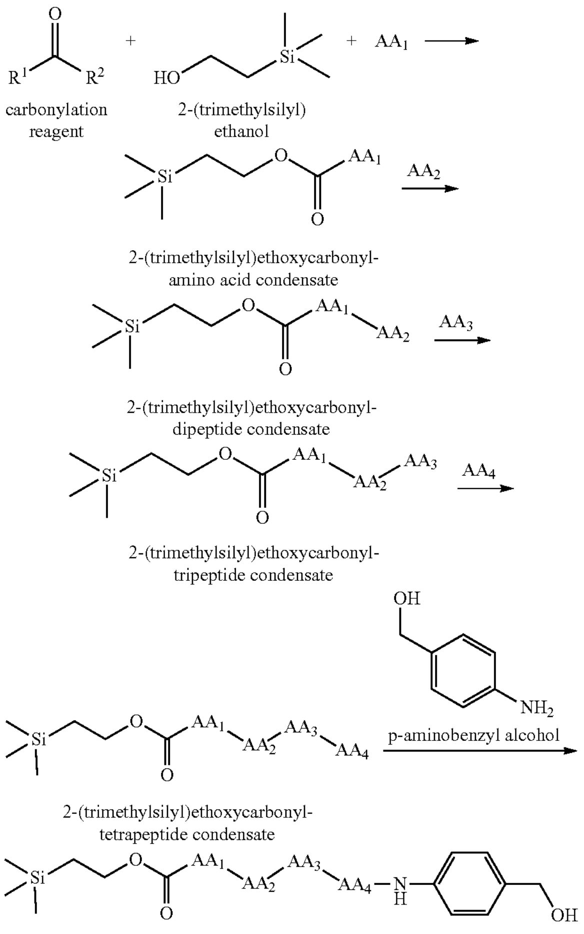

2-(trimethylsilyl)ethoxycarbonyl-tetrapeptide-p-aminobenzyl alcohol condensate (3)

wherein the preparation method comprises the following steps:
1) performing a condensation reaction between a carbonylation reagent, 2-(trimethylsilyl)ethanol and amino acid $AA_1$ to obtain a 2-(trimethylsilyl)ethoxycarbonyl-amino acid condensate;
2) performing a condensation reaction between the 2-(trimethylsilyl)ethoxycarbonyl-amino acid condensate and amino acid $AA_2$ to obtain a 2-(trimethylsilyl)ethoxycarbonyl-dipeptide condensate;
3) performing a condensation reaction between the 2-(trimethylsilyl)ethoxycarbonyl-dipeptide condensate and amino acid $AA_3$ to obtain a 2-(trimethylsilyl)ethoxycarbonyl-tripeptide condensate;
4) performing a condensation reaction between the 2-(trimethylsilyl)ethoxycarbonyl-tripeptide condensate and amino acid $AA_4$ to obtain a 2-(trimethylsilyl)ethoxycarbonyl-tetrapeptide condensate; and
5) performing a condensation reaction between the 2-(trimethylsilyl)ethoxycarbonyl-tetrapeptide condensate and p-aminobenzyl alcohol to obtain a 2-(trimethylsilyl)ethoxycarbonyl-tetrapeptide-p-aminobenzyl alcohol condensate.

The present invention further provides a method for preparing the oligopeptide linker intermediate of formulae (4), wherein the reaction route of the method is as follows: performing a condensation reaction between a carbonylation reagent, 2-(trimethylsilyl)ethanol and amino acid $AA_1$, amino acid $AA_2$, amino acid $AA_3$ and amino acid $AA_4$ in sequence, to obtain a 2-(trimethylsilyl)ethoxycarbonyl-tetrapeptide condensate, wherein the carbonylation reagent is any compound containing a carbonyl group.

Further, the oligopeptide linker intermediate of formula (4) is obtained via the following reaction route:

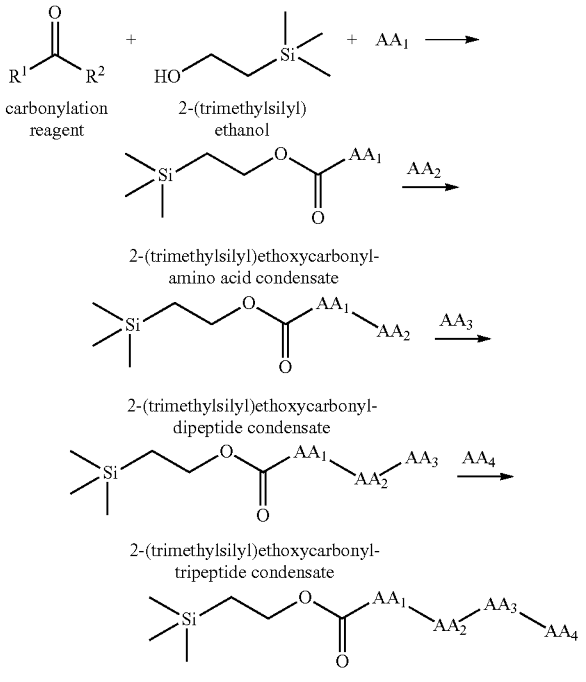

2-(trimethylsilyl)ethoxycarbonyl-tetrapeptide condensate (4)

1) performing a condensation reaction between a carbonylation reagent, 2-(trimethylsilyl)ethanol and amino acid $AA_1$ to obtain a 2-(trimethylsilyl)ethoxycarbonyl-amino acid condensate;
2) performing a condensation reaction between the 2-(trimethylsilyl)ethoxycarbonyl-amino acid condensate and amino acid $AA_2$ to obtain a 2-(trimethylsilyl)ethoxycarbonyl-dipeptide condensate;

3) performing a condensation reaction between the 2-(trimethylsilyl)ethoxycarbonyl-dipeptide condensate and amino acid $AA_3$ to obtain a 2-(trimethylsilyl)ethoxycarbonyl-tripeptide condensate; and 4) performing a condensation reaction between the 2-(trimethylsilyl)ethoxycarbonyl-tripeptide condensate and amino acid $AA_4$ to obtain a 2-(trimethylsilyl)ethoxycarbonyl-tetrapeptide condensate.

Further, the carbonylation reagent has a structure of formula (5):

(5)

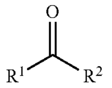

wherein:

the $R_1$ and $R_2$ are independently selected from the group consisting of:

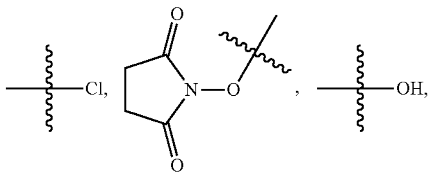

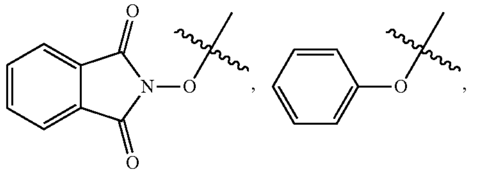

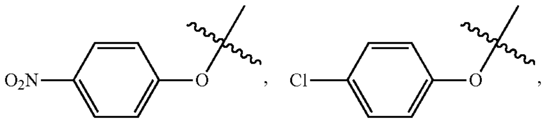

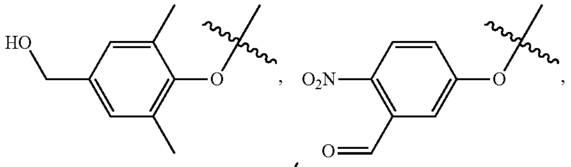

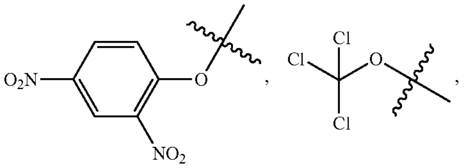

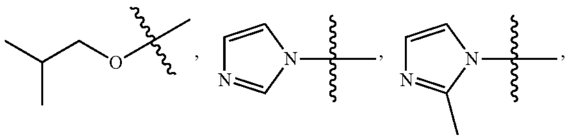

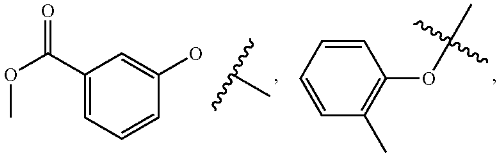

and

-continued

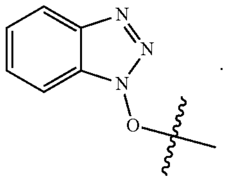

Furthermore, the carbonylation reagent is selected from the group consisting of:

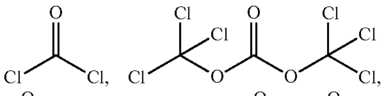

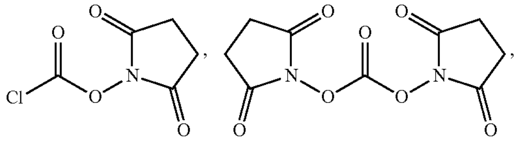

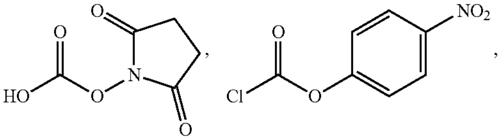

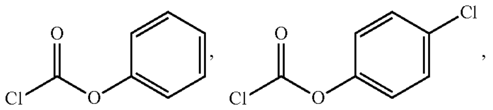

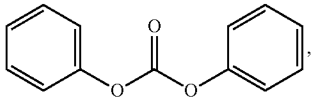

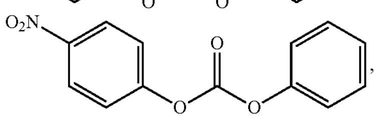

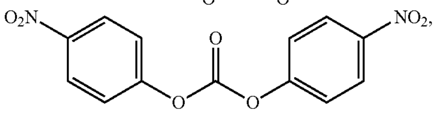

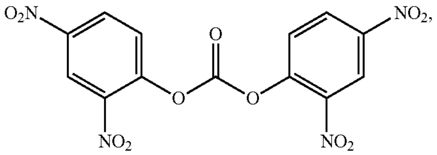

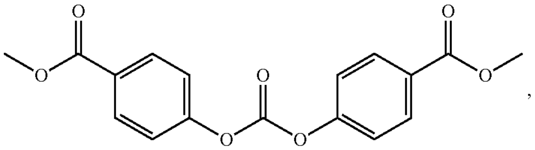

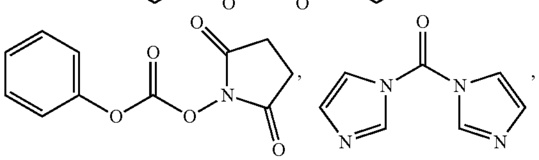

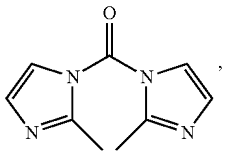

and

-continued

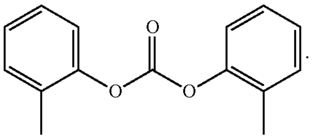

Further, the $AA_1$, $AA_2$, $AA_3$, and $AA_4$ are independently selected from the group consisting of -valine- -citrulline -(-Cit-), -alanine- (-Ala-), -lysine- (-Lys-), lysine(trityl)- (-Lys(Trt)-), -lysine(monomethoxytrityl)- (-Lys(Mmt)-), -lysine(fluorenylmethyloxycarbonyl)- (-Lys(Fmoc)-), -arginine- (-Arg-), -phenylalanine- (-Phe-), -glycine- (-Gly-), -leucine- (-Leu-), and -isoleucine- (-Ile-).

Furthermore, the $-AA_1-AA_2-$ is selected from -valine-citrulline- -valine-alanine- (-Val-Ala-), -valine-lysine- (-Val-Lys-), -valine-lysine(trityl)- (-Val-Lys(Trt)-), -valine-lysine (monomethoxytrityl)- (-Val-Lys(Mmt)-), -valine-lysine (fluorenylmethyloxycarbonyl)- (-Val-Lys(Fmoc)-), -valine-arginine- (-Val-Arg-), -phenylalanine-citrulline- (-Phe-Cit-), -phenylpropyl-lysine- (-Phe-Lys-), -phenylalanine-lysine (trityl)- (-Phe-Lys(Trt)-), -phenylalanine-lysine (monomethoxytrityl)- (-Phe-Lys (Mmt)-), -phenylalanine-lysine (fluorenylmethyloxycarbonyl)- (-Phe-Lys(Fmoc)-), leucine-citrulline- (-Leu-Cit-), isoleucine-citrulline (-Ile-Cit-) and -phenylalanine-arginine-(-Phe-Arg-); the $-AA_1-AA_2-AA_3-$ is selected from -phenylalanine-arginine-arginine-(-Ala-Arg-Arg-); the $-AA_1-AA_2-AA_3-AA_4-$ is selected from the group consisting of -glycine-glycine-phenylalanine-glycine- (-Gly-Gly-Phe-Gly-), -glycine-phenylalanine-leucine-glycine- (-Gly-Phe-Leu-Gly-), and -alanine-leucine-alanine-leucine (-Ala-Leu-Ala-Leu-).

Preferably, the $-AA_1-AA_2-$ is selected from the following structures:

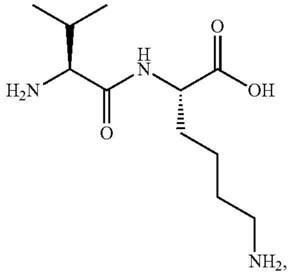

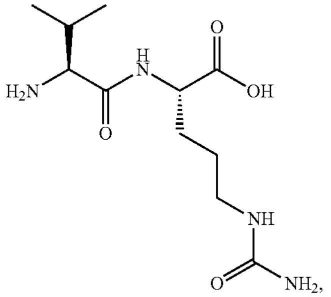

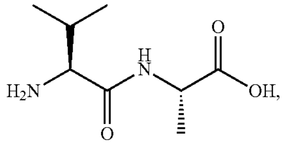

-continued

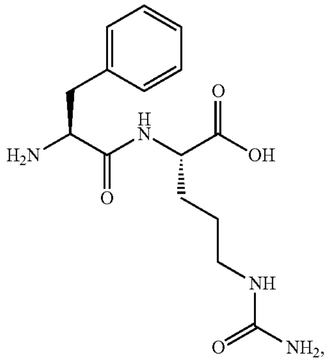

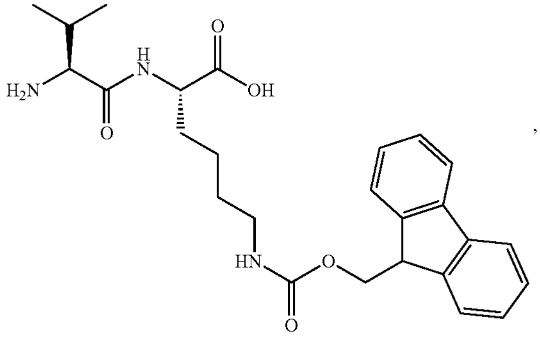

,

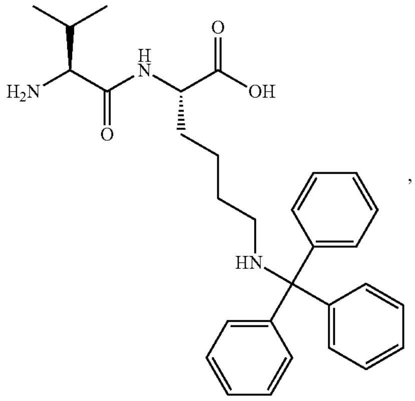

,

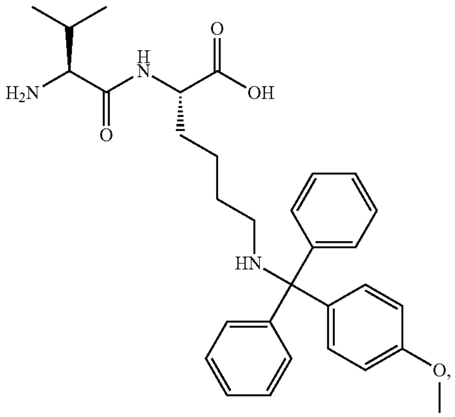

-continued
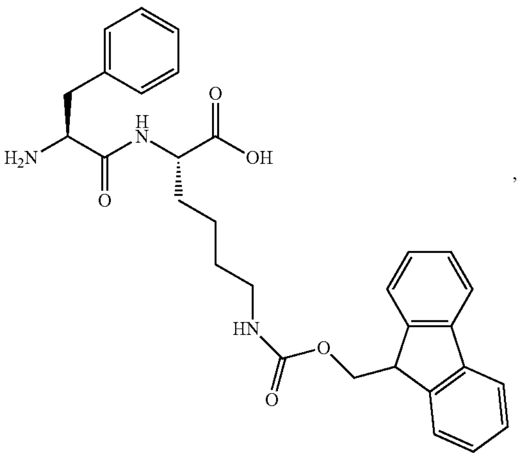
,
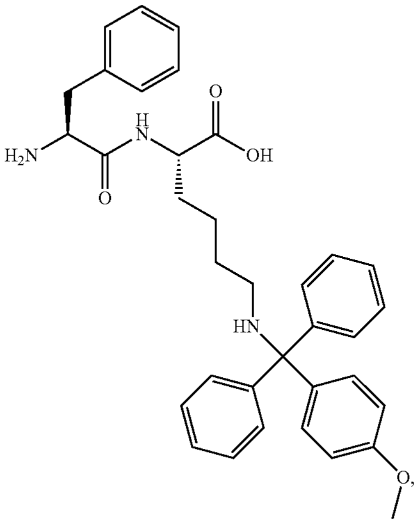
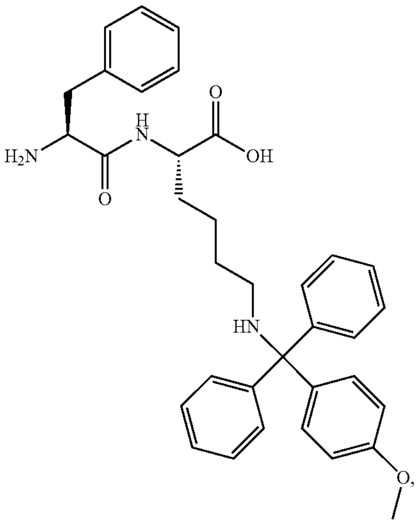
-continued
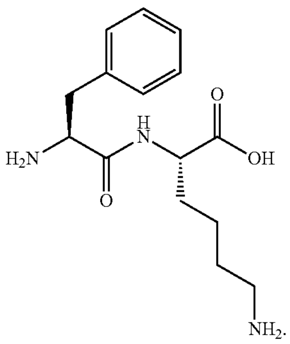
Preferably, the $-AA_1-AA_2-AA_3-$ is selected from the following structures:
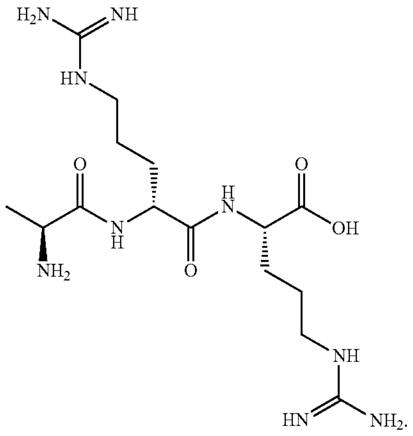 [SMILES: C[C@H](N)C(=O)N[C@H](CCCNC(=N)N)C(=O)N[C@@H](CCCNC(=N)N)C(=O)O]
Preferably, the $-AA_1-AA_2-AA_3-AA_4-$ is selected from the following structures:
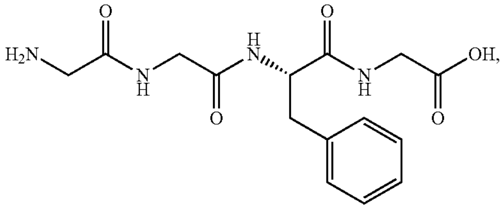
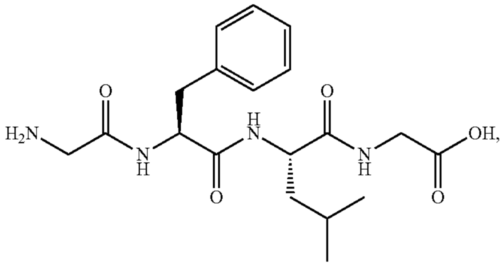

-continued

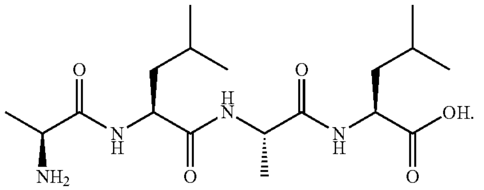

The present invention further provides the use the intermediate according to any one of the foregoing contents in the preparation of an antibody drug conjugate.

Further, the solvent used in the condensation reaction described above is any polar solvent or non-polar solvent; preferably, the solvent is one or more selected from the group consisting of tetrahydrofuran, dioxane, acetonitrile, DMF, DMSO, DMAc, DMPU, HMPA, ethylene glycol dimethyl ether, diethyl ether, tert-butyl methyl ether, tert-butanol, water, ethyl acetate, methanol, ethanol, isopropanol, dichloromethane, chloroform, and carbon tetrachloride; more preferably, the solvent is one or more selected from the group consisting of tetrahydrofuran, dioxane, acetonitrile, DMF, DMSO, water, methanol, dichloromethane, chloroform, carbon tetrachloride and ethanol.

In some specific embodiments, when performing a condensation reaction between an carbonylation reagent with 2-(trimethylsilyl)ethanol and amino acid $AA_1$, the reagent used in the condensation reaction is preferably one or more selected from the group consisting of tetrahydrofuran, dioxane, acetonitrile, DMF, DMSO, DMAc, DMPU, HMPA, ethylene glycol dimethyl ether, diethyl ether, tert-butyl methyl ether, tert-butanol, water and ethyl acetate; more preferably, the reagent is one or more selected from the group consisting of tetrahydrofuran, dioxane, acetonitrile, DMF, DMSO and water.

In another specific embodiments, after the reaction of the carbonylation reagent with 2-(trimethylsilyl)ethanol and amino acid $AA_1$, the reagent used in the condensation reaction of the 2-(trimethylsilyl)ethoxycarbonyl-amino acid condensate and $AA_2$, and further with $AA_3$ and/or $AA_4$ in another embodiments, is one or more selected from the group consisting of tetrahydrofuran, dioxane, acetonitrile, DMF, DMSO, DMAc, DMPU, HMPA, methanol, ethanol, isopropanol, ethylene glycol dimethyl ether, diethyl ether, tert-butyl methyl ether, tert-butanol, water and ethyl acetate; more preferably, the reagent is one or more selected from the group consisting of tetrahydrofuran, dioxane, acetonitrile, DMF, DMSO, water and methanol.

In another specific embodiments, after the above reactions, when performing a condensation reaction between the polypeptide condensate (i.e., 2-(trimethylsilyl)ethoxycarbonyl-dipeptide condensate, 2-(trimethylsilyl)ethoxycarbonyl-tripeptide condensate, 2-(trimethylsilyl)ethoxycarbonyl-tetrapeptide condensate) with p-aminobenzyl alcohol, the reagent used in the condensation reaction is preferably one or more selected from the group consisting of dichloromethane, chloroform, carbon tetrachloride, methanol, ethanol, isopropanol, tetrahydrofuran, dioxane, acetonitrile, DMF, DMSO, DMAc, DMPU, HMPA, ethylene glycol dimethyl ether, diethyl ether, tert-butyl methyl ether, tert-butanol and ethyl acetate; more preferably, the reagent is one or more selected from the group consisting of dichloromethane, chloroform, carbon tetrachloride, methanol, ethanol and DMF.

The present invention also provides a use of the method according to any one of the foregoing contents in the preparation of an antibody-drug conjugate.

The preparation of antibody-drug conjugates further comprises the process of removing Teoc protection:

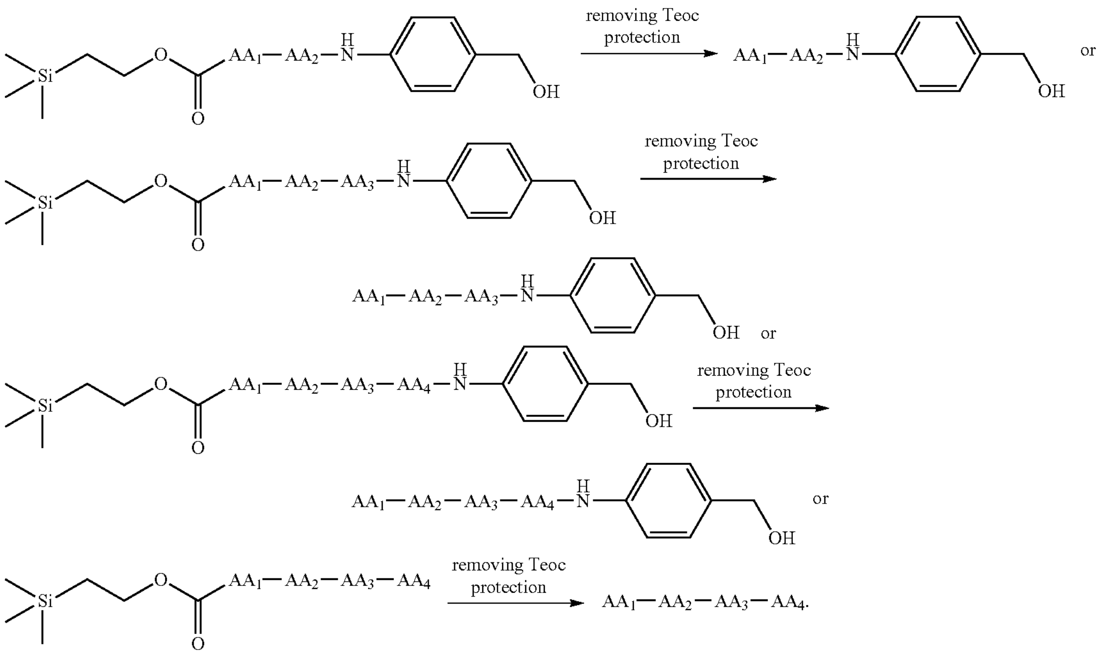

The product obtained by removing Teoc protection as described above is often used as part of the linker to be covalently linked to the drug moiety in the preparation of antibody-drug conjugate. In order to achieve covalent linking to the antibody moiety, the said product is often coupled with a connector via the following specific reaction routes:
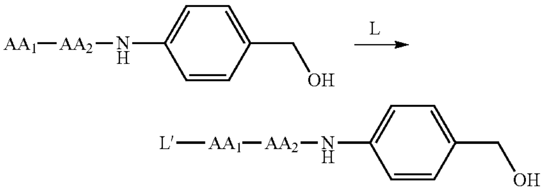
or
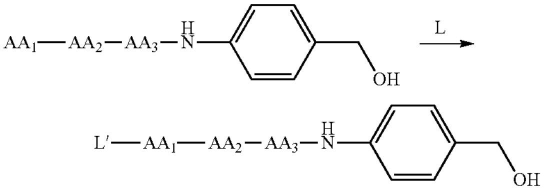
or
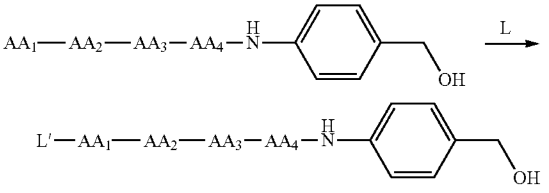
or
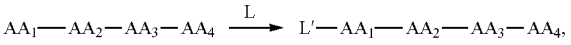
wherein, L and L' are connectors, and can be any linking group.
In some embodiments, the connector L is selected from:
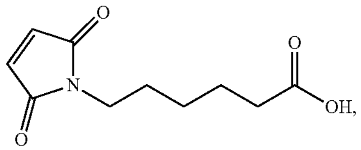
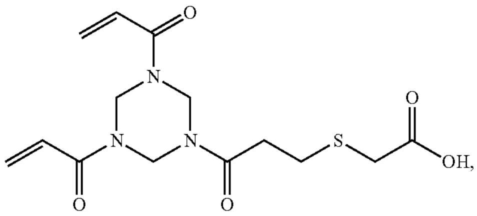
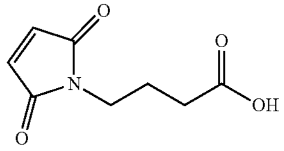
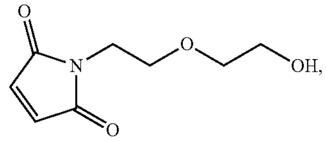
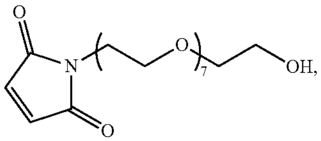
-continued
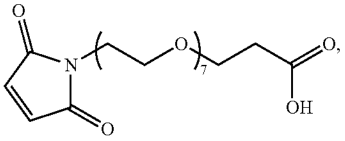
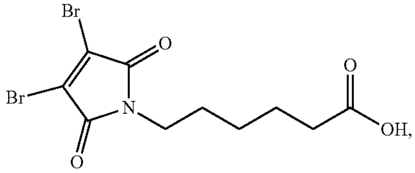
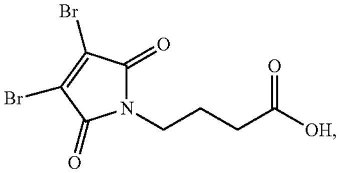
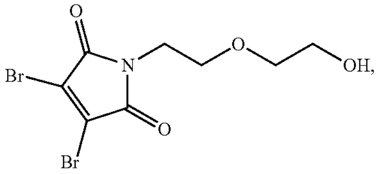
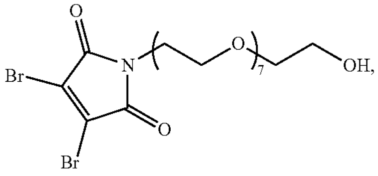
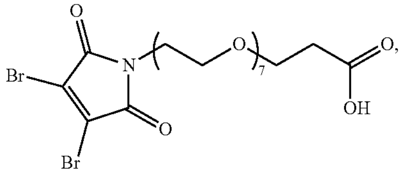
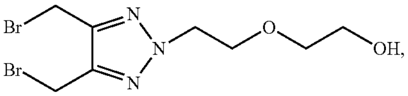
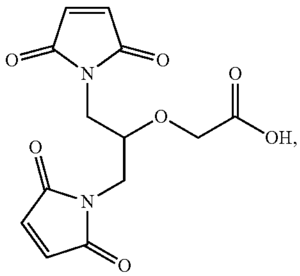
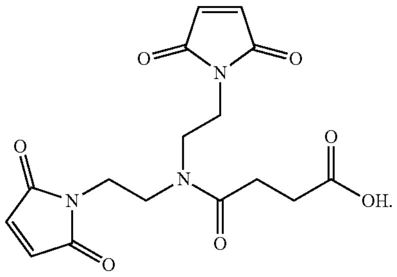

Accordingly, the linking group L' is selected from:
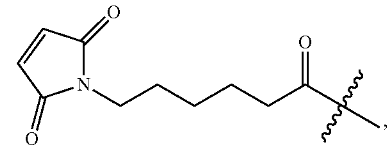
,
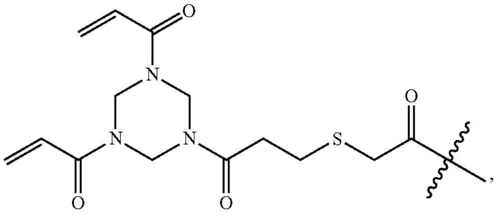
,
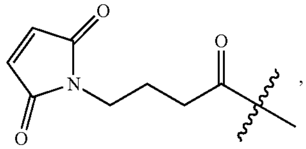
,
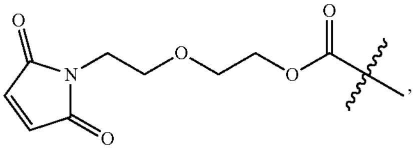
,
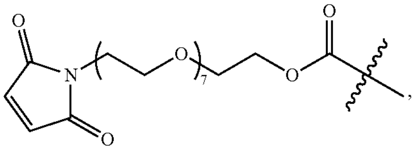
,
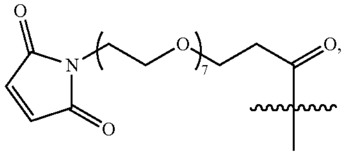
,
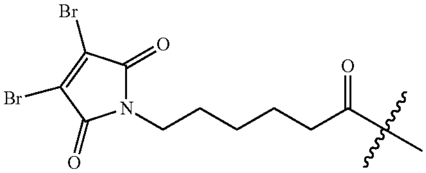
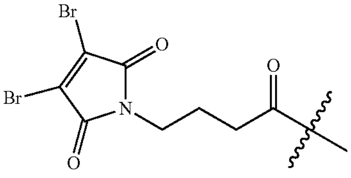
-continued
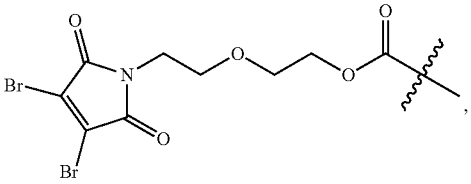
,
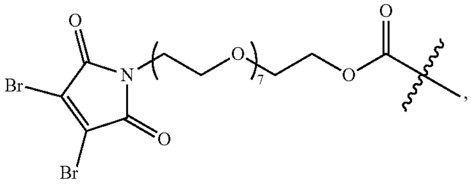
,
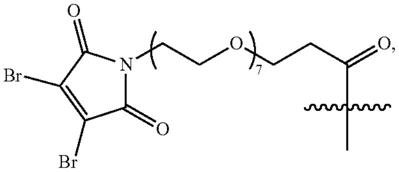
,
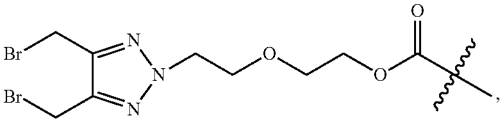
,
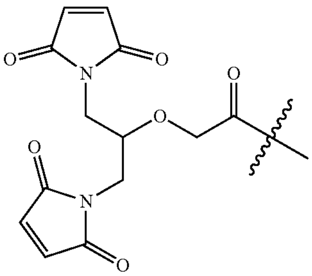
,
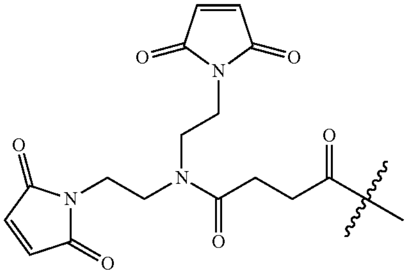
.
In a specific embodiment, the oligopeptide linker is selected from:
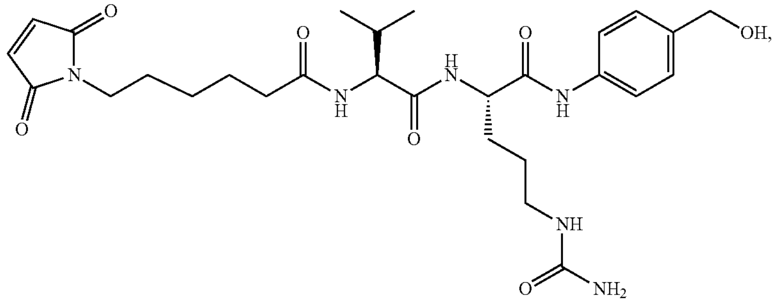
, -continued
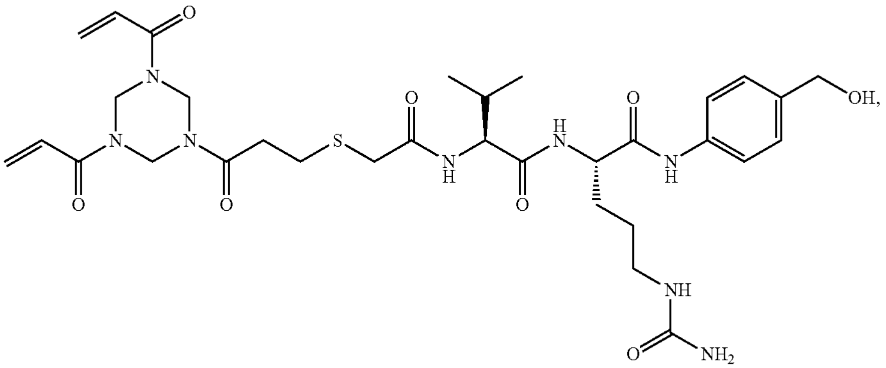
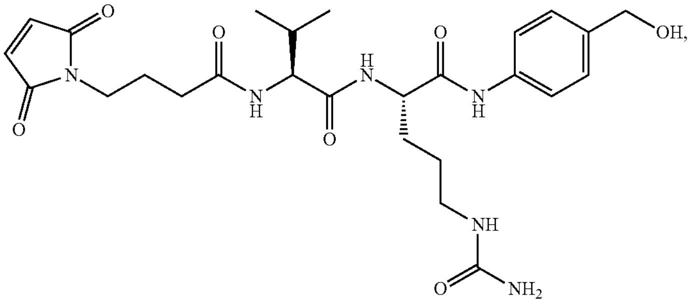
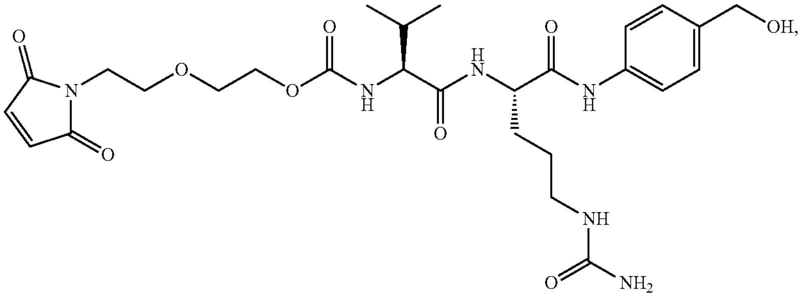
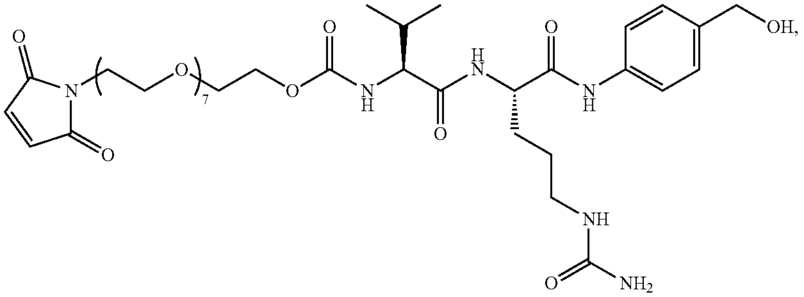
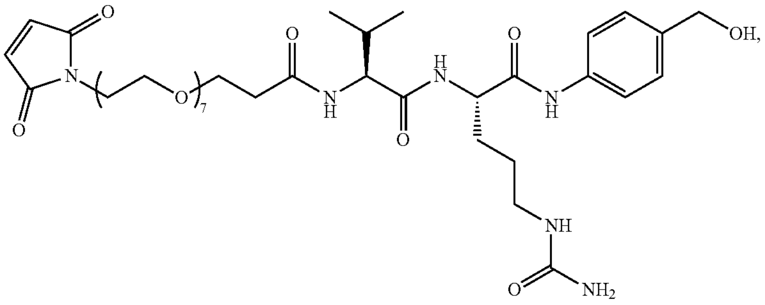

-continued
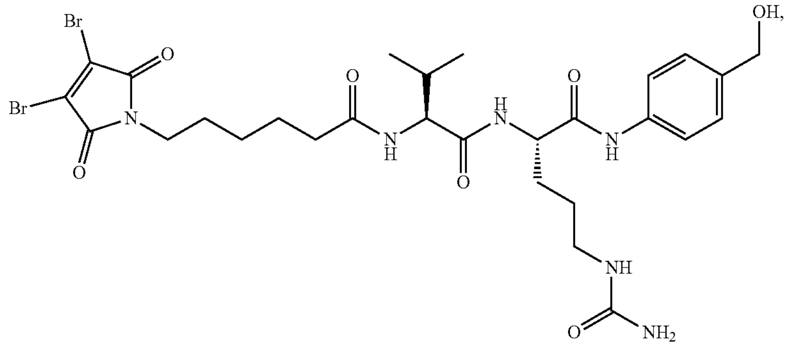
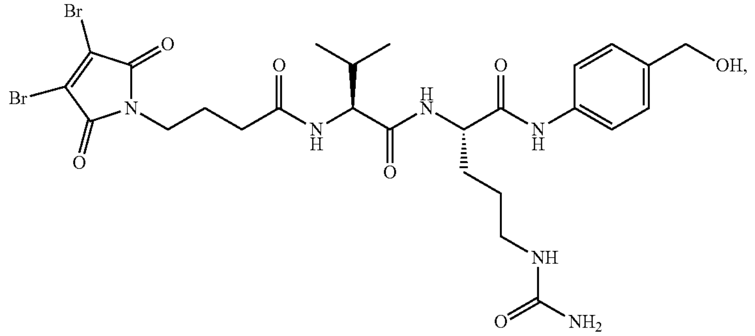
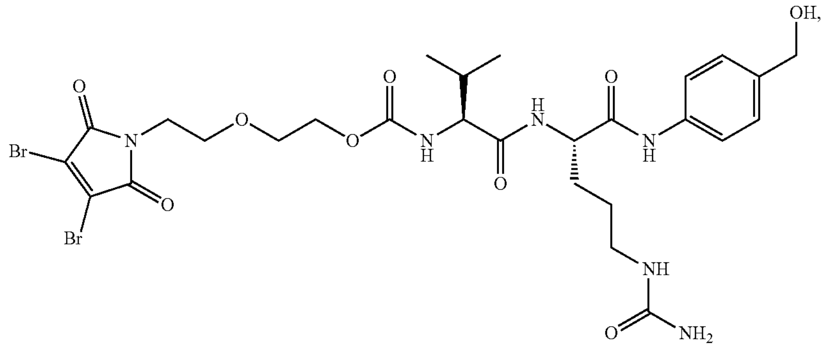
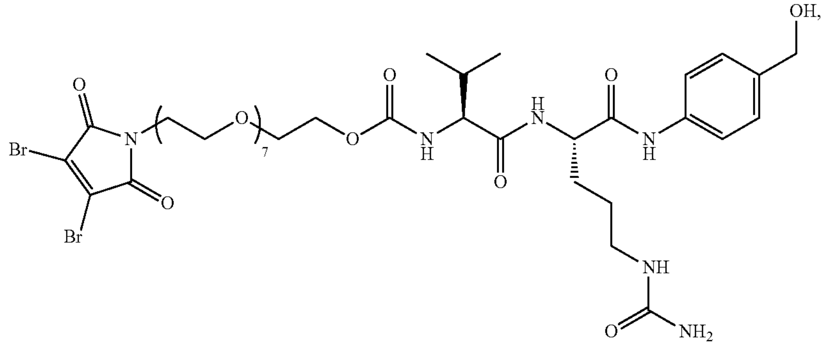
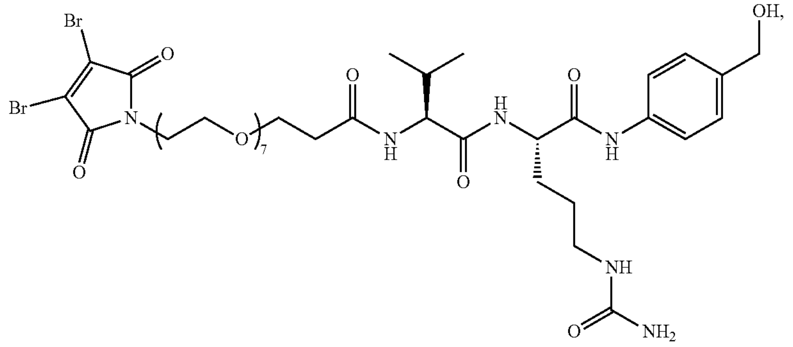

-continued
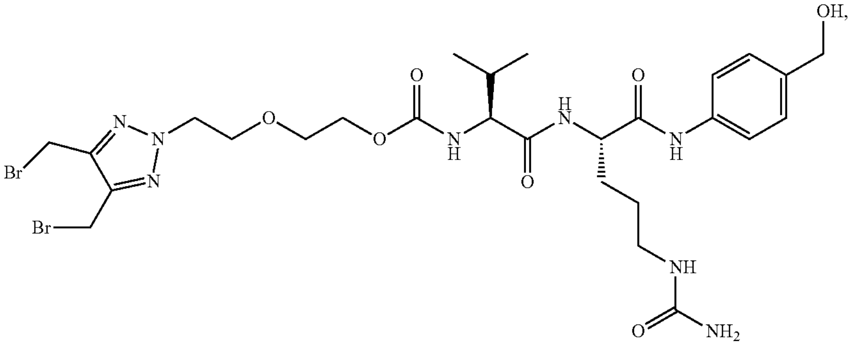
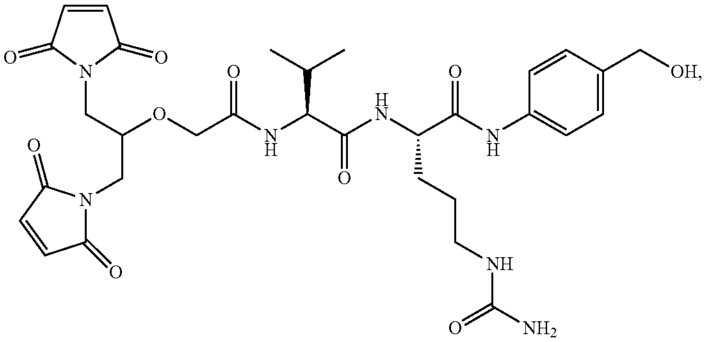
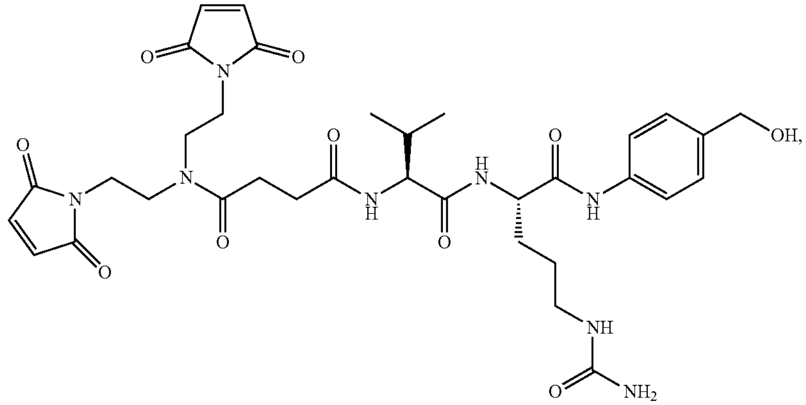
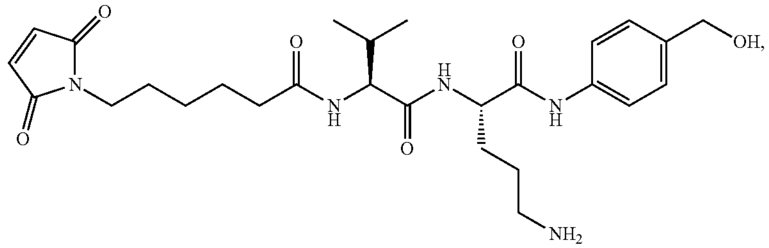
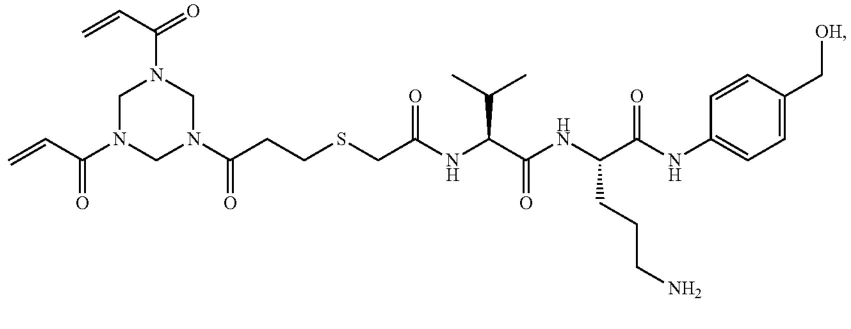

-continued
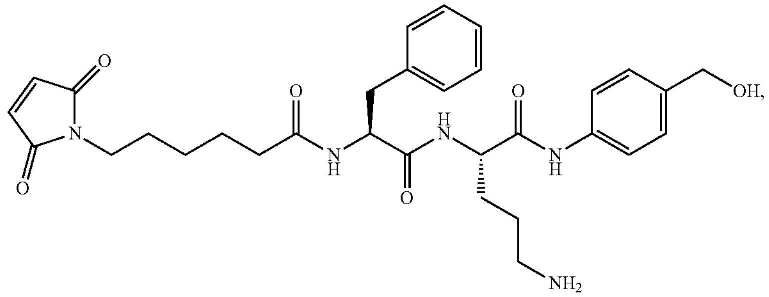,
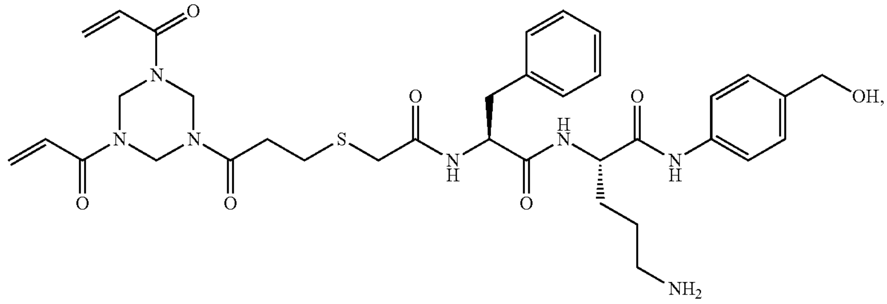,
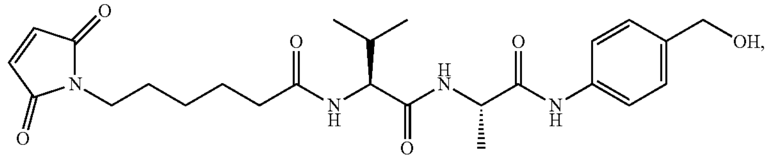,
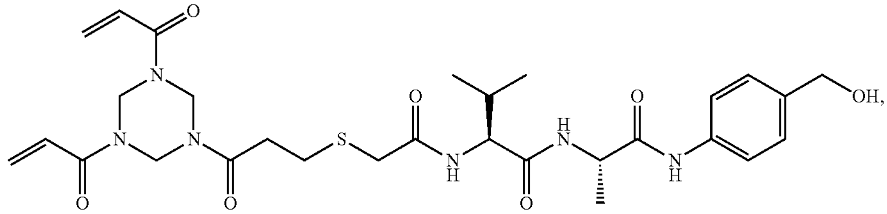,
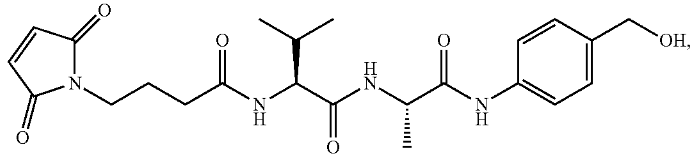,
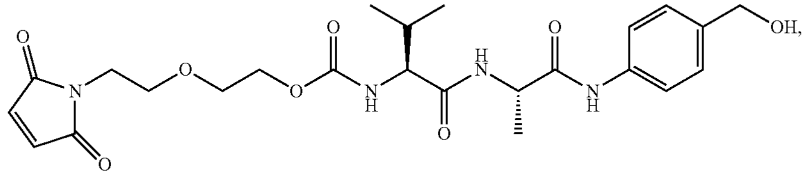,
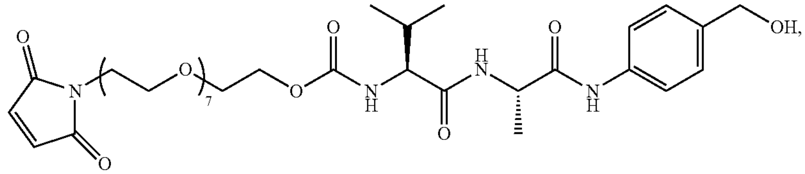,
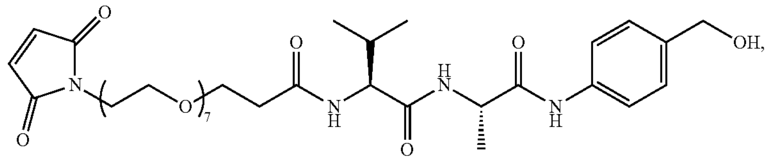, -continued
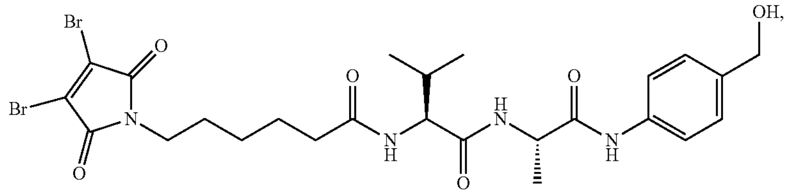
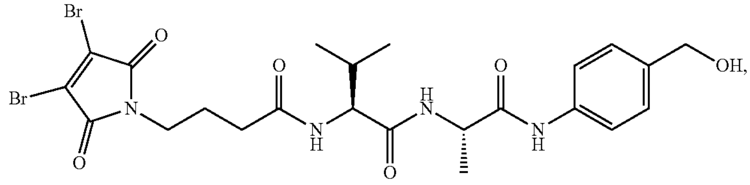
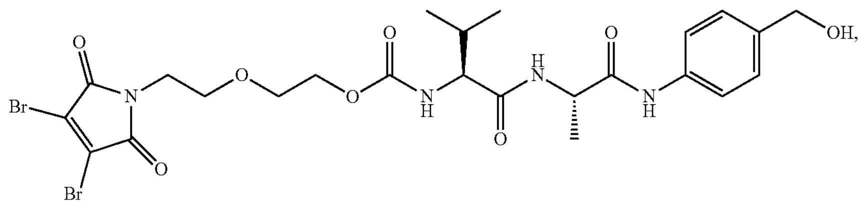
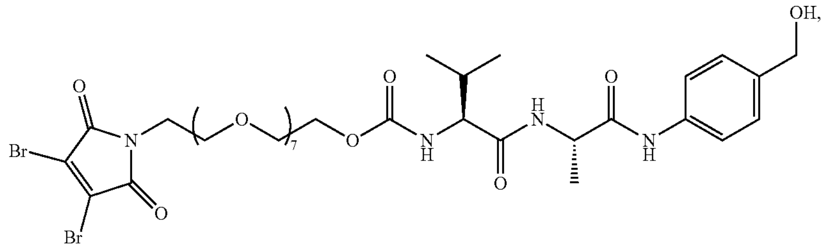
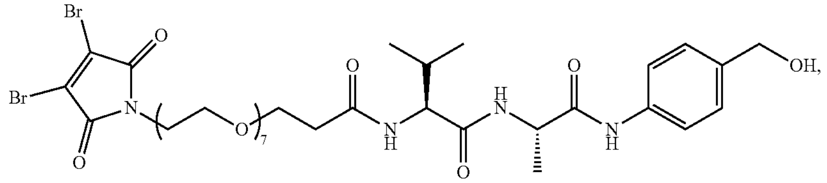
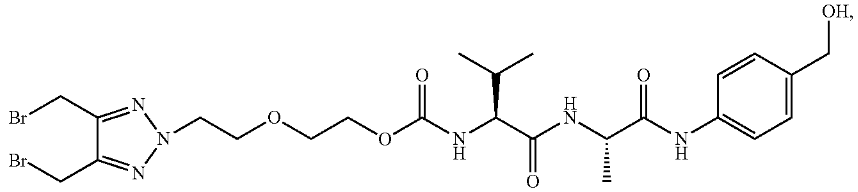
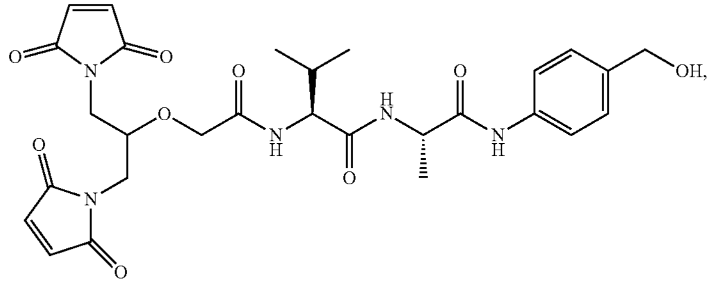

-continued

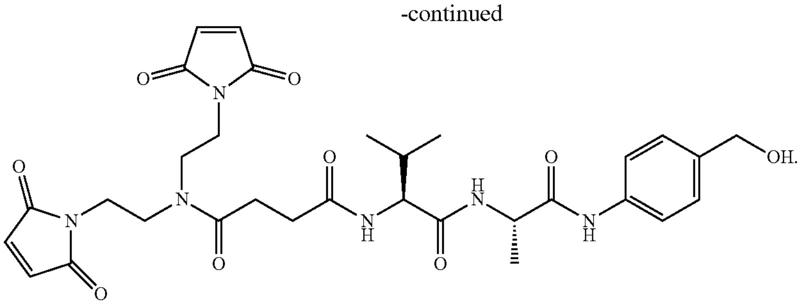

BRIEF DESCRIPTION OF THE FIGURE

FIGS. 1-A to 1-F show the relevant LC-MS diagrams of the Val-Cit-PAB prepared by Teoc protecting group method, in which FIG. 1-A is a mass spectrum of the blank control, F1-B is a liquid phase spectrum of the blank control, FIG. 1-C is a mass spectrum of the Val-Cit-PAB prepared by Teoc protecting group method, FIG. 1-D is a liquid phase spectrum of the product, FIG. 1-E is a positive ion mass spectrum of the product, and FIG. 1-F is a negative ion mass spectrum of the product.

FIG. 2-A to FIG. 2-H show relevant LC-MS diagrams of the Val-Cit-PAB prepared by Cbz protecting group method, in which FIG. 2-A is a mass spectrum of the blank control, FIG. 2-B is a liquid phase spectrum of the blank control, FIG. 2-C is a mass spectrum of the Val-Cit-PAB prepared by Cbz protecting group method, FIG. 2-D is a liquid phase spectrum of the product, FIG. 2-E is a positive ion mass spectrum of the product, FIG. 2-F is a negative ion mass spectrum of the product, FIG. 2-G is a ion mass spectrum of the impurity, and FIG. 2-H is a negative ion mass spectrum of the impurity.

FIG. 3-A to FIG. 3-D show relevant LC-MS diagrams of the Val-Cit-BAB prepared by Boc protecting group method (hydrochloric acid deprotection method), in which FIG. 3-A is a mass spectrum of the Val-Cit-PAB prepared by Boc protecting group method, FIG. 3-B is a liquid phase spectrum of the product, FIG. 3-C is a positive ion spectrum, and FIG. 3-D is a negative ion spectrum.

FIG. 4-A to FIG. 4-D show relevant LC-MS diagrams of the Val-Cit-PAB prepared by Boc protecting group method (trifluoroacetic acid deprotection method), in which FIG. 4-A is a mass spectrum of the Val-Cit-PAB prepared by Boc protecting group method, FIG. 4-B is a liquid phase spectrum of the product, FIG. 4-C is a positive ion spectrum, and FIG. 4-D is a negative ion spectrum.

DETAILED DESCRIPTION OF THE INVENTION

Abbreviation

Unless otherwise stated, all abbreviations used in the present invention have the same meaning as understood by those of ordinary skill in the art. As used in the present invention, the common abbreviations and their definitions are as follows:

| Abbreviation | Definition |
|---|---|
| Fmoc | fluorenylmethyloxycarbonyl |
| Cbz | carbobenzyloxy |
| Boc | tert-butoxycarbonyl |

-continued

| Abbreviation | Definition |
|---|---|
| Teoc | 2-(trimethylsilyl)ethoxycarbonyl |
| Val | valine |
| Cit | citrulline |
| Ala | alanine |
| Lys | lysine |
| Arg | arginine |
| Phe | phenylalanine |

Definition

Various terms related to various aspects of the specification are used throughout the specification and claims. Unless otherwise indicated, such terms are given their ordinary meaning in the art. Other specifically defined terms should be understood in a manner consistent with the definitions provided herein.

As used herein, the terms “a” and “an” and “the” are used in accordance with standard practice and mean one or more, unless the context indicates otherwise. Thus, for example, reference to “an antibody drug conjugate” includes a combination of two or more antibody drug conjugates and the like.

It should be understood that wherever an aspect is described herein with the word, “comprising” it also provides similar aspects described with “consisting of” and/or “substantially consisting of”.

Although the numerical ranges and parameter approximations shown in the broad scope of the present invention, the numerical values shown in the specific examples are described as accurately as possible. However, any numerical value inherently must contain a certain amount of error, which is caused by the standard deviation present in their respective measurements. In addition, all ranges disclosed herein are understood to cover any and all subranges contained therein. For example, a recorded range of “1 to 10” should be considered to include any and all subranges between a minimum of 1 and a maximum of 10 (inclusive); that is, all subranges beginning with a minimum of 1 or greater, such as 1 to 6.1, and subranges ending with a maximum of 10 or less, such as 5.5 to 10. In addition, any reference referred to as “incorporated herein” is to be understood as being incorporated in its entirety.

As used in the present invention,  means that the group containing  connected to another group through a chemical bond here.

The term “linking group” used in the present invention refers to a bifunctional or multifunctional molecule, which can react with a protein/antibody molecule and a dipeptide linker, respectively, and thus function as a "bridge" to link the protein/antibody with the dipeptide linker.

The term "oligopeptide linker" used in the present invention generally refers to a linking structure containing two or more amino acid residues, which further comprises a p-benzyl alcohol residue. The two amino acids are linked together by means of dehydration condensation. The amino acids referred to herein generally refer to those organic compounds containing both amino and carboxyl groups, including all essential amino acids and non-essential amino acids. Preferably, the amino acid includes, but is not limited to, -valine- (-Val-), -citrulline -(-Cit-), -alanine- (-Ala-), -lysine- (-Lys-), -lysine(trityl)- (-Lys(Trt)-), -lysine (monomethoxytrityl)- (-Lys(Mmt)-), -lysine(fluorenylmethyloxycarbonyl)- (-Lys(Fmoc)-), -arginine- (-Arg-), -phenylalanine- (-Phe-), -glycine- (-Gly-), -leucine- (-Leu-), and -isoleucine- (-Ile-).

SPECIFIC EXAMPLES

The following further describes the present invention in combination with specific examples. It should be understood that these examples are only used to illustrate the present invention and not to limit the scope of the present invention. The experimental methods without specific conditions in the following examples are generally performed under conventional conditions or conditions recommended by the manufacturer. The reagents without specific sources are conventional reagents purchased on the market. Unless otherwise stated, all percentages, ratios, proportions, or parts are by weight.

The units in weight-volume percentage in the present invention are well known to those skilled in the art, and for example, refer to the weight of a solute in 100 ml of a solution.

Unless otherwise defined, all specialties and sciences used herein are used in the same sense as those familiar to those skilled in the art. In addition, any method or material similar or equal to the content described can be used in the method of the present invention. The preferred embodiments and materials described herein are for illustration purposes only.

Example 1 Preparation of Val-Cit-PAB by Teoc Protecting Group Method

(1) Preparation of Teoc-Val-Cit

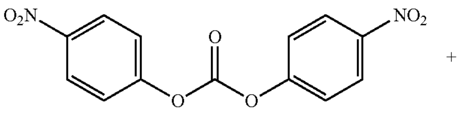

bis(4-nitrophenyl)carbonate

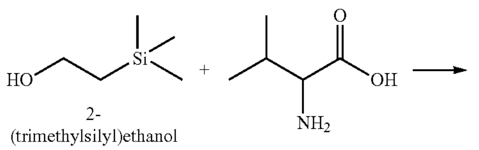

2-(trimethylsilyl)ethanol

L-valine

-continued

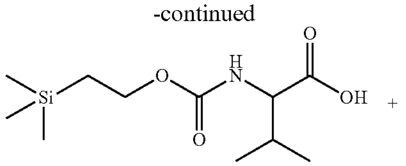

2-(trimethylsilyl)ethoxycarbonyl-L-valine

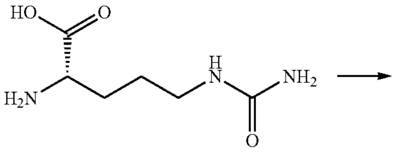

L-citrulline

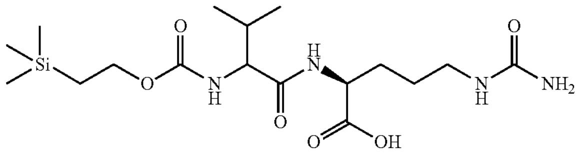

2-(trimethylsilyl)ethoxycarbonyl-L-valyl-L-citrulline 14.16 g of 2-(trimethylsilyl)ethanol (120 mmol), 38.7 g of N,N-diisopropylethylamine (300 mmol), 30.4 g of bis(4-nitrophenyl)carbonate (100 mmol), and 400 mL of acetonitrile were sequentially added into a 500 mL single-neck flask. After the addition, the mixture was stirred at room temperature for 16 h to form reaction solution 1. 14.08 g of L-valine (120 mmol) and 25.8 g of N,N-diisopropylethylamine (200 mmol) were added into a 1 L single-neck flask, and dissolved in 400 mL of water to form reaction solution 2. The reaction solution 1 was added to the reaction solution 2 with stirring, and after stirring at room temperature for 16 h, the completion of the reaction was detected by LC-MS method. After passing the detection, the reaction solution was rotary evaporated to remove the solvent. After evaporation, 500 mL of water was added, and 1 mol/L hydrochloric acid was added dropwise with stirring to adjust the pH to 1. Then, the aqueous phase was extracted twice, each with 300 mL of ethyl acetate. The extracts were combined and washed twice, each with 300 mL of water. After washing with water, the extract was dried by adding anhydrous magnesium sulfate, and the solvent was rotary evaporated to obtain 54 g of a pale yellow viscous solid product (i.e., 2-(trimethylsilyl)ethoxycarbonyl-L-valyl mixture containing 4-nitrophenol (simply referred to as 2-(trimethylsilyl)ethoxycarbonyl-L-valyl mixture)). LC-MS (M–H)–: 260.1. The 2-(trimethylsilyl)ethoxycarbonyl-L-valyl mixture was used in the next reaction without purification.

10.5 g of the 2-(trimethylsilyl)ethoxycarbonyl-L-valyl mixture (40 mmol) as prepared above, 24.3 g of N,N,N',N'-tetramethyl-O—(N-succinimide)urea tetrafluoroborate (80 mmol), 25.8 g N,N-diisopropylethylamine (200 mmol), and 200 mL N,N-dimethylformamide were sequentially added into a 500 mL single-necked flask. After the addition, the mixture was stirred at room temperature for 6 h to form reaction solution 3.21 g of L-citrulline (120 mmol) was added into a 1 L single-neck flask, and completely dissolved under stirring with the addition of 400 mL of water, to form a reaction solution 4. 15.5 g of N,N-diisopropylethylamine (120 mmol) and 200 mL of N,N-dimethylformamide were added into a 500 mL beaker, to form a reaction solution 5. The reaction solution 5 was added to the reaction solution 4, then transferred to a low-temperature bath, and stirred at –10° C. for 0.5 h. Then, the reaction solution 3 was slowly added dropwise to the above reaction system under stirring at –10° C., which was controlled to be completed in about 2 h. After the completion of the addition, the mixture was kept at −10° C. for 16 h under stirring. Then, the completion of the reaction was detected by LC-MS method. After passing the detection, the system was rotary evaporated to remove the solvent, and after rotary evaporation, 500 mL of 0.1 mol/L hydrochloric acid was added and stirred well. The aqueous phase was extracted twice, each with 300 mL of ethyl acetate. The extracts were combined and washed twice, each with 300 mL 0.1 mol/L hydrochloric acid, and then washed twice with 300 mL of water. After washing with water, the extract was dried by adding anhydrous magnesium sulfate, and the solvent was rotary evaporated before 100 mL of ethyl acetate and 1000 mL of toluene were added with stirring for 16 h and then filtered. The filter cake was dissolved in 50 mL of THF, and 1 L of methyl tert-butyl ether:n-hexane=1:1 was added to prepare a solution. The mixture was stirred at room temperature for 16 hours and then filtered. The filter cake was dissolved in 50 mL of THF before 1 L of toluene was added. After stirring at room temperature for 6 h, the mixture was filtered and the filter cake was dried to obtain 11.1 g of an off-white powdery solid product with a yield of 68%. LC-MS$(M+H)^+$: 418.7, LC-MS $(M-H)^-$: 416.7.

(2) Preparation of Teoc-Val-Cit-PAB

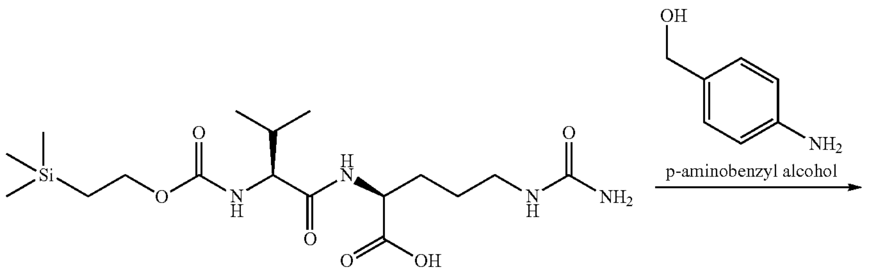

2-(trimethylsilyl)ethoxycarbonyl-L-valyl-L-citrulline

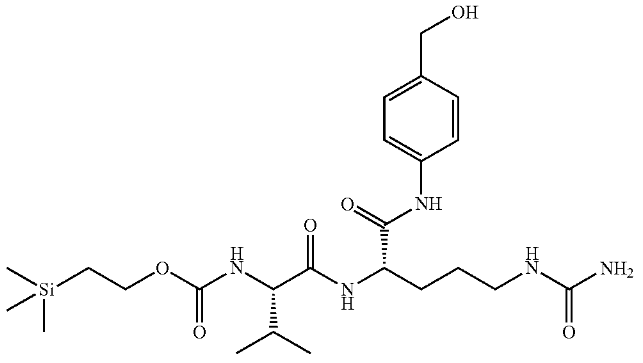

2-(trimethylsilyl)ethoxycarbonyl-L-valyl-L-citrull amido-p-benzyl alcohol 7.5 g of 2-(trimethylsilyl)ethoxycarbonyl-L-valyl-L-citrulline (18 mmol), 9 g of N-ethoxyacyl-2-ethoxy-1,2-dihydroquinoline (36 mmol), 4.5 g of p-aminobenzyl alcohol (36 mmol), 150 mL of dichloromethane and 75 mL of methanol were sequentially added into a 500 mL single-neck flask. After the addition, the mixture was stirred at room temperature for 16 h. Then, the completion of the reaction was detected by LC-MS method. After passing the detection, the reaction solution was dried by rotary evaporation, and after evaporation, 200 mL of dichloromethane and 200 mL of ethyl acetate were added and stirred for 16 h, and then filtered. To the filter cake, 100 mL of dichloromethane, 100 mL of ethyl acetate, and 200 mL of n-hexane were added with stirring for 16 h, and then filtered. The filter cake was dried to obtain 7.5 g of an off-white powdery solid product (the product was 2-(trimethylsilyl)ethoxycarbonyl-L-valyl-L-citrull amido-p-benzyl alcohol, namely Teoc-Val-Cit-PAB) with a yield of 80%. LC-MS$(M+H)^+$: 523.5, LC-MS $(M-H)^-$: 522.

(3) Preparation of Val-Cit-PAB (Relative Molecular Weight: 379.46)

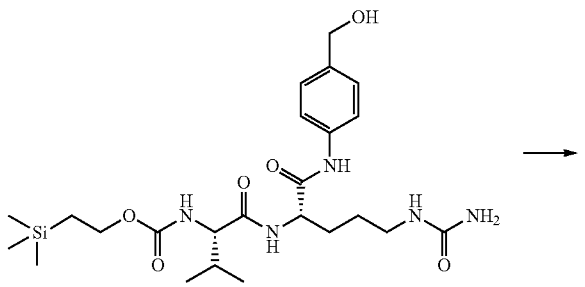

2-(trimethylsilyl)ethoxycarbonyl-L-valyl-L-citrull amido-p-benzyl alcohol

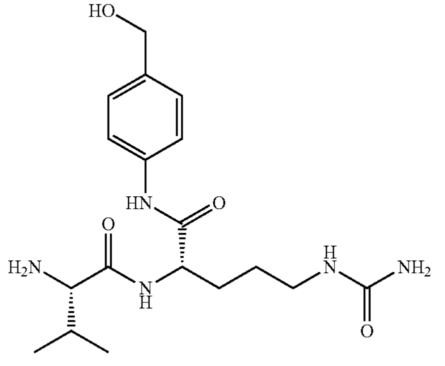

L-valyl-L-citrull amido-p-benzyl alcohol 3.15 g of 2-(trimethylsilyl)ethoxycarbonyl-L-valyl-L-citrull amido-p-benzyl alcohol (6.2 mmol), 2.16 g of potassium fluoride (37.2 mmol), 12.4 mL of a 1.0 mol/L tetrabutylammonium fluoride solution in tetrahydrofuran, and 100 mL of N,N-dimethylformamide were sequentially added into a 500 mL single-necked flask. After the addition, the mixture was stirred at room temperature for 24 h and then the completion of the reaction was detected by LC-MS method. After the completion of the reaction, the reaction solution was filtered. After rotatory evaporation of the solvent of the filtrate, 100 mL of anhydrous ethanol was added to fully dissolve the residue. 18 mL of a 1 mol/L dilute hydrochloric acid solution was added and stirred well before the mixture was dried by adding anhydrous magnesium sulfate and then filtered. The filtrate was dried by rotary evaporation, and then 30 mL of ethanol was added to completely dissolve the residue. Under stirring at room temperature, a mixed solution of 200 mL of methyl tert-butyl ether and 200 mL of dichloromethane was added and stirred for 1 h before filtered. The filter cake was dried to obtain 1.83 g of an off-white powdery solid product (the product was L-valyl-L-citrull amido-p-benzyl alcohol, that is, Val-Cit-PAB) with a yield of 80%.

In the LC-MS detection, FIG. 1-A is a mass spectrum of the blank control, F1-B is a liquid phase spectrum of the blank control, FIG. 1-C is a mass spectrum of the Val-Cit-PAB prepared by Teoc protecting group method (the product in this example), FIG. 1-D is a liquid phase spectrum of the product, FIG. 1-E is a positive ion mass spectrum of the product, and FIG. 1-F is a negative ion mass spectrum of the product. By comparing FIG. 1-A with FIG. 1-C, it can be seen that the peak at the time point of 2.87 min is the product ion peak. By comparing FIG. 1-B with FIG. 1-D, it can be seen that the product has a strong HPLC signal, and by combining with FIG. 1-A and FIG. 1-C, it can be seen that the Val-Cit-PAB prepared by the Teoc protecting group method has fewer impurities. By analyzing the positive ion detection spectrum (2.849 min) and negative ion detection spectrum (2.866 min) at 2.87 min, it can be known that: LC-MS$(M+H)^+$: 379.6, LC-MS$(M-H)^-$: 378.0.

Example 2 Preparation of Val-Cit-PAB by Cbz Protecting Group Method (1) Preparation of Cbz-Val-Cit

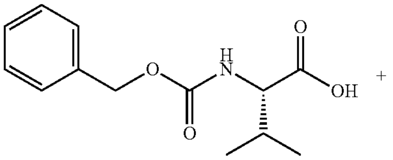

N-benzyloxycarbonyl-L-valine

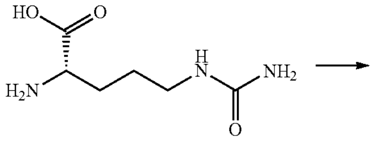

L-citrulline

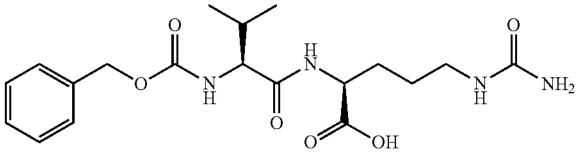

N-benzyloxycarbonyl-L-valyl-L-citrulline 10 g of N-benzyloxycarbonyl-L-valine (i.e., Cbz-Val) (40 mmol), 18.2 g of N,N,N',N'-tetramethyl-O—(N-succinimide)urea tetrafluoroborate (60 mmol), 15.5 g of N,N-diisopropylethylamine (120 mmol), and 300 mL of acetonitrile were sequentially added into a 1 L single-neck flask. After the addition, the mixture was stirred at room temperature for 4 h. After dissolving 7.7 g of L-citrulline (44 mmol) in 300 ml of water, the mixture was added to the above reaction system and stirred at room temperature for 16 h. Samples were taken for detection by LC-MS, and then the reaction was completed. Under stirring, 0.1 mol/L hydrochloric acid was added dropwise to adjust the pH to 1. After the solvent was dried by rotary evaporation, 800 mL of water was added, stirred at room temperature for 16 h, and filtered. After the filter cake was dried under vacuum, 400 mL of ethyl acetate and 400 mL of dichloromethane were added and stirred for 16 h before filtered. After the filter cake was dried under vacuum, 200 mL of ethyl acetate, 200 mL of dichloromethane, and 400 mL of n-hexane were added, and the mixture was stirred for 16 hours and then filtered. The filter cake was dried to obtain 12.65 g of an off-white powdery solid product (i.e., N-benzyloxycarbonyl-L-valyl-L-citrulline) with a yield of 77%. LC-MS$(M+H)^+$: 408.7, LC-MS$(M-H)^-$: 406.9.

(2) Preparation of Cbz-Val-Cit-PAB

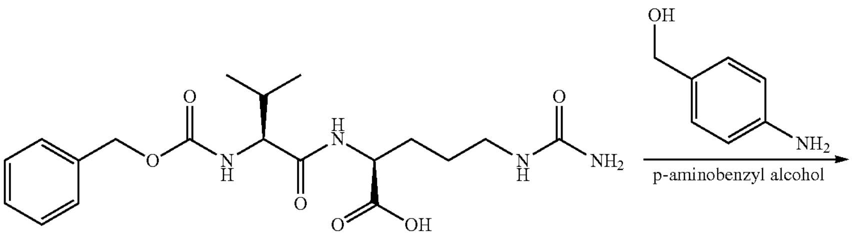

N-benzyloxycarbonyl-L-valyl-L-citrulline

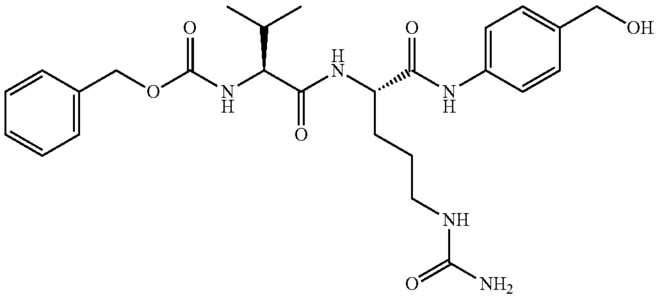

N-benzyloxycarbonyl-L-valyl-L-citrull amido-p-benzyl alcohol 12.65 g of N-benzyloxycarbonyl-L-valyl-L-citrulline (31 mmol), 15.74 g of N-ethoxyacyl-2-ethoxy-1,2-dihydroquinoline (62 mmol), 7.53 g of p-aminobenzyl alcohol (62 mmol), 200 ml, of dichloromethane, and 100 mL of methanol were sequentially added into a 500 mL single-neck flask. After stirring at room temperature for 16 h, samples were taken for detection by LC-MS, and then the reaction was completed. After the reaction solution was dried by rotary evaporation, 200 mL of dichloromethane and 200 mL of ethyl acetate were added, stirred for 16 h, and filtered, 100 mL of dichloromethane, 100 mL of ethyl acetate, and 200 mL of n-hexane were added to the filter cake, stirred for 16 h and filtered. The filter cake was dried to obtain 9.1 g of an off-white powdery solid product with a vied of 60%. LC-MS $(M+H)^+$: 513.6.

(3) Preparation of Val-Cit-PAB (Relative Molecular Weight: 379.46)

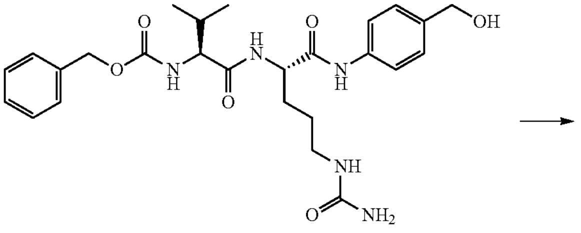

N-benzyloxycarbonyl-L-valyl-L-citrull amido-p-benzyl alcohol

-continued

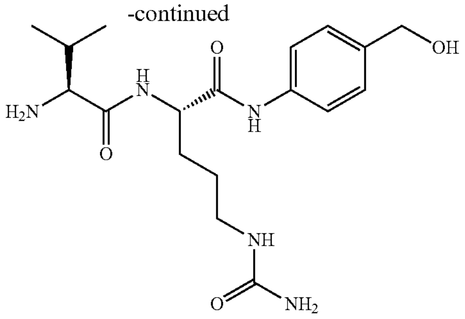

L-valyl-L-citrull amido-p-benzyl alcohol 1.12 g of N-benzyloxycarbonyl-L-valyl-L-citrull amido-p-benzyl alcohol (2 mmol), 0.3 g of palladium on carbon, and 100 mL of methanol were sequentially added into a 250 mL single-neck flask and stirred at 10° C. The reaction system was covered with a balloon filled with hydrogen gas, and the mixture was stirred at 10° C. for 16 h. Samples were taken for detection by LC-MS, and then the reaction was completed. The reaction solution was filtered, and the filtrate was dried by rotary evaporation. 400 mL of n-hexane was added, stirred for 16 h, and then filtered. The filter cake was dried to obtain 0.69 g of an off-white powdery solid product with a yield of 91%.

In the LC-MS detection, FIG. 2-A is a mass spectrum of the blank control, FIG. 2-B is a liquid phase spectrum of the blank control, FIG. 2-C is a mass spectrum of the Val-Cit-PAB prepared by Cbz protecting group method (the product in this example), FIG. 2-D is a liquid phase spectrum of the product, FIG. 2-E is a positive ion mass spectrum of the product, FIG. 2-F is a negative ion mass spectrum of the product, FIG. 2-G is a ion mass spectrum of the impurity, and FIG. 2-H is a negative ion mass spectrum of the impurity. By Comparing FIG. 2-A with FIG. 2-C, it can be seen that there are two stronger ion peaks: at 4.33 min and at 6.54 min. By comparing FIGS. 2-B and 2-D, it can be seen that there are two peaks with strong HPLC signals at 4.12 min and at 5.39 min, and combining with FIG. 2-A and FIG. 2-C, it can be inferred that one of the two peaks is a product peak and one is an impurity peak, and the content of impurities is higher. By analyzing the positive ion mass spectrum and negative ion mass spectrum at 4.33 min and at 5.54 min, it can be found that the peak at 4.33 min is the product peak (LC-MS$(M+H)^+$: 379.6, LC-MS$(M-H)^-$: 378.0), and the peak at 5.54 min is the impurity peak (LC-MS$(M+H)^+$: 363.6), which is speculated to be a by-product of Val-Cit-PAB dehydroxylation (with a molecular weight difference of only 16), and its content is higher. Since the chemical properties of the by-product are very similar to the product, the by-product is very hard to be removed, and has a great effect on the subsequent reactions and product quality. In addition, hydrogen gas is used as a reactant in the deprotection process, which poses a safety risk.

Example 3 Preparation of Phe-Cit-PAB by Boc Protecting Group Method (1) Preparation of Boc-Phe-Cit

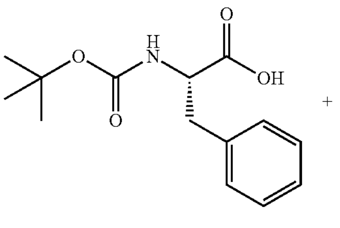

N-(tert-butoxycarbonyl)-L-phenylalanine

-continued

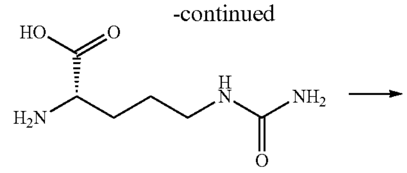

L-citrulline

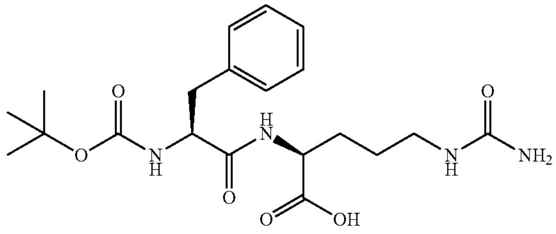

N-(tert-butoxycarbonyl)-L-phenylalanyl-L-citrulline 2.65 g of N-(tert-butoxycarbonyl)-L-phenylalanine (10 mmol) (i.e., Boc-Phe), 3.61 g of N,N,N',N'-tetramethyl-O—(N-succinimide)urea tetrafluoroborate (12 mmol), 3.87 g of N,N-diisopropylethylamine (30 mmol), and 50 mL of N,N-dimethylformamide were sequentially added into a 250 mL single-neck flask, and stirred at room temperature for 4 h.

1.75 g of L-citrulline (10 mmol) was dissolved in 50 ml of water, which is added to the above reaction system and stirred at room temperature for 16 h. Samples were taken for detection by LC-MS, and then the reaction was completed. Under stirring, 0.1 mol/L hydrochloric acid was added dropwise to adjust the pH to 1. After the system was dried by rotary evaporation, 200 mL of water was added, stirred at room temperature for 16 h, and filtered. After the filter cake was dried, 100 mL of ethyl acetate and 100 mL of dichloromethane were added, stirred for 16 h and filtered. The filter cake was dried to obtain 3 g of a yellow powdery solid product (that is, N-(tert-butoxycarbonyl)-L-phenylalanyl-L-citrulline, Boc-Phe-Cit) with a yield of 71%. LC-MS $(M-H)^-$: 421.4.

(2) Preparation of Boc-Phe-Cit-PAB

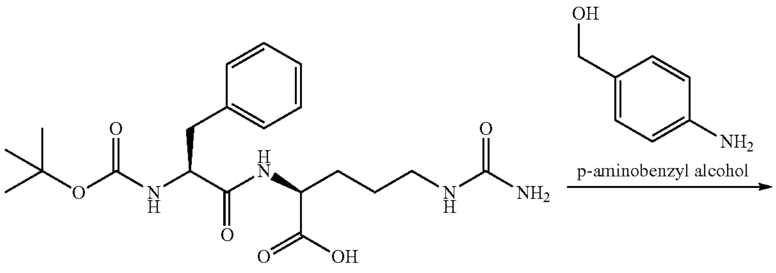

N-(tert-butoxycarbonyl)-L-phenylalanyl-L-citrulline

-continued

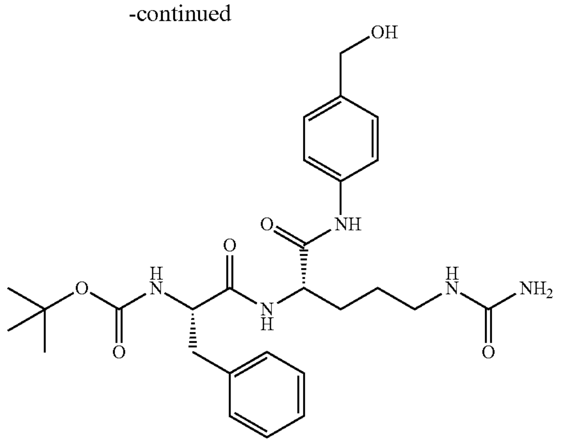

N-(tert-butoxycarbonyl)-L-phenylalanyl-L-citrull amido-p-benzyl alcohol 3 g of N-(tert-butoxycarbonyl)-L-phenylalanyl-L-citrulline (7.1 mmol) (i.e., Boc-Phe-Cit), 3.5 g of N-ethoxyacyl-2-ethoxy-1,2-dihydroquinoline (14.2 mmol), 1.75 g of p-aminobenzyl alcohol (14.2 mmol), 60 mL of dichloromethane, and 30 mL of methanol were sequentially added into a 250 mL single-neck flask, and stirred at room temperature for 16 h. Then samples were taken for detection by LC-MS, and then the reaction was completed. After the reaction solution was dried by rotary evaporation, 100 mL of dichloromethane and 100 mL of ethyl acetate were added, stirred for 16 h, and centrifuged. 100 mL of n-hexane was added to the white solid in the lower layer, stirred for 2 h and centrifuged. The white solid in the lower layer was dried to obtain 2.3 g of a off-white powdery solid product (that is, N-(cert-butoxycarbonyl)-L-phenylalanyl-L-citrull amido-p-benzyl alcohol, Boc-Phe-Cit-PAB) with a yield of 62%. LC-MS$(M-H)^-$: 526.2.

(3) Preparation of Phe-Cit-PAB (Relative Molecular Weight: 427.51)

The Boc protecting group is removed by hydrochloric acid deprotection and trifluoroacetic acid deprotection, respectively, shown as follows.

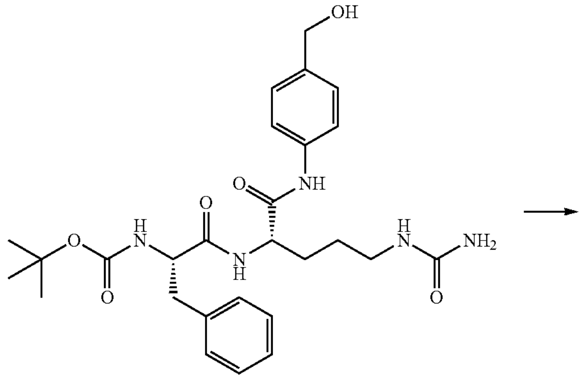

N-(tert-butoxycarbonyl)-L-phenylalanyl-L-citrull amido-p-benzyl alcohol

-continued

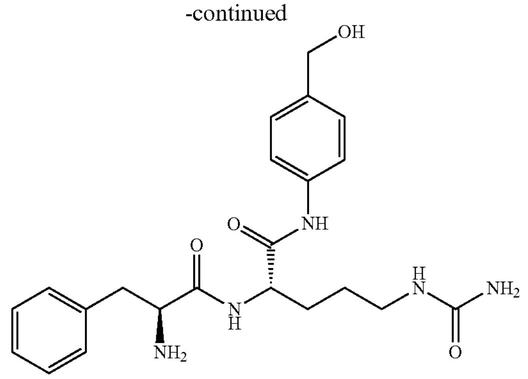

L-phenylalanyl-L-citrull amido-p-benzyl alcohol (a) Hydrochloric Acid Deprotection Method 0.5 g of N-(tert-butoxycarbonyl)-L-phenylalanyl-p-benzyl alcohol (1 mmol) (i.e., Boc-Phe-Cit-PAB), 3 mL of 4 mol/L hydrogen chloride solution in dioxane and 3 mL of dioxane were sequentially added into a 10 mL single-neck flask. After the addition, the mixture was stirred at room temperature for 3 h. Samples were taken for detection by LC-MS, and then the reaction was completed.

In the LC-MS detection, FIG. 3-A is a mass spectrum of the Phe-Cit-PAB prepared by Boc protecting group method (the product in this example), FIG. 3-B is a liquid phase spectrum of the product, FIG. 3-C is a positive ion spectrum, and FIG. 3-D is a negative ion spectrum. It can be seen from FIG. 3-A that there is a strong ion peak at 5.39 min. By analyzing the positive ion mass spectrum (5.390 min) and negative ion mass spectrum (5.403 min) at this position, the value of LC-MS$(M+H)^+$: 446.2, LC-MS$(M-H)^-$: 444.1 was obtained. It is speculated that most of the products prepared by this method are by-products in which the hydroxyl group at the benzyl position is replaced by chlorine.

(b) Trifluoroacetic Acid Deprotection Method 0.5 g of N-(tert-butoxycarbonyl)-L-phenylalanyl-L-citrull amido-p-benzyl alcohol (1 mmol) and 3 mL of trifluoroacetic acid were sequentially added into a 10 mL single-neck flask. After the addition, the mixture was stirred at room temperature for 2 h and the completion of the reaction was detected by LC-MS.

In the LC-MS detection, FIG. 4-A is a mass spectrum of the Phe-Cit-PAB prepared by Boc protecting group method (the product in this example), FIG. 4-B is a liquid phase spectrum of the product, FIG. 4-C is a positive ion spectrum, and FIG. 4-D is a negative ion spectrum. It can be seen from FIG. 4-A that there is a strong ion peak at 5.77 min. By analyzing the positive ion mass spectrum (5.768 min) and negative ion mass spectrum (5.781 min) at this position, the value of LC-MS$(M+H)^+$: 524.4, LC-MS$(M-H)^-$: 522.1 was obtained. It is speculated that most of the products prepared by this method are by-products in which the hydroxyl group at the benzyl position forms trifluoroacetate.

In summary, the method for preparing Val-Cit-PAB using Teoc as a protecting group provided by the present invention is easily carried out under mild reaction conditions, and since almost no side reactions occur in the reaction, the method produces a high-purity product with fewer impurities and easy to be purified. The method for preparing Val-Cit-PAB using Cbz as a protecting group produces large amounts of by-products from dehydroxylation. Because the chemical properties of the by-products are very similar to the products, they are very difficult to be removed, greatly affecting the subsequent reactions and product quality. In addition, hydrogen gas is used as a reactant in the deprotection process, which poses a safety risk. The method of preparing Val-Cit-PAB by using Boc as a protecting group has the problems that the hydroxyl group at the benzyl position is replaced by chlorine, and forms trifluoroacetate in a high conversion rate. Therefore, compared with the other two methods, the Teoc method provided by the present invention can be easily carried out and produces few impurities, thus achieving unexpected technical effects.

| Protecting group | By-products | | Easy or difficult to purify | Reaction conditions |
|---|---|---|---|---|
| Teoc | — | very few | easy | mild |
| Cbz | By-products from dehydroxylation of Val-Cit-PAB | more | difficult | Use of hydrogen poses safety risks |
| Boc | By-products in which the hydroxyl group at the benzyl position of Val-Cit-PAB is replaced by chlorine | most | difficult | Use of large amounts of acid presents safety risks and is not environmentally friendly. |
| | By-products in which the hydroxyl group at the benzyl position of Val-Cit-PAB forms trifluoroacetate | most | difficult | |

The invention has been exemplified by various specific embodiments. However, those of ordinary skill in the art can understand that the present invention is not limited to the specific embodiments. Those of ordinary skill in the art can make various changes or modifications within the scope of the present invention, and various technical features mentioned in various places in this specification can be combined with each other without departing from the spirit and scope of the present invention. Such modifications and variations are all within the scope of the present invention.

The invention claimed is:

1. A method for preparing the oligopeptide linker intermediate of formula (1), wherein the oligopeptide linker intermediate of formula (1) is obtained via the following reaction path:

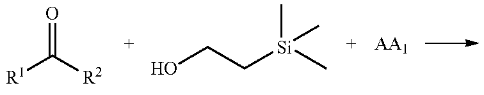

carbonylation reagent 2-(trimethylsilyl) ethanol

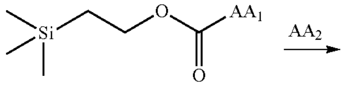

2-(trimethylsilyl)ethoxycarbonyl-amino acid condensate

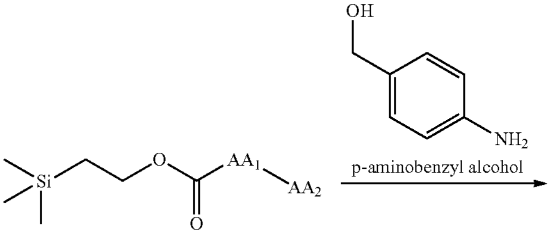

2-(trimethylsilyl)ethoxycarbonyl-dipeptide condensate

-continued

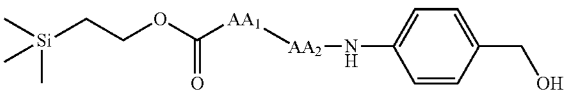

2-(trimethylsilyl)ethoxycarbonyl-dipeptide-p-aminobenzyl alcohol condensate (1)

wherein the method comprises the following steps:

1) performing a condensation reaction between a carbonylation reagent, 2-(trimethylsilyl)ethanol and amino acid $AA_1$ to obtain a 2-(trimethylsilyl)ethoxycarbonyl-amino acid condensate;

2) performing a condensation reaction between the 2-(trimethylsilyl)ethoxycarbonyl-amino acid condensate and amino acid $AA_2$ to obtain a 2-(trimethylsilyl)ethoxycarbonyl-dipeptide condensate; and 3) performing a condensation reaction between the 2-(trimethylsilyl)ethoxycarbonyl-dipeptide condensate and p-aminobenzyl alcohol to obtain a 2-(trimethylsilyl)ethoxycarbonyl-dipeptide-p-aminobenzyl alcohol condensate;

wherein the amino acid $AA_1$ is valine, the amino acid $AA_2$ is citrulline; and the carbonylation reagent is

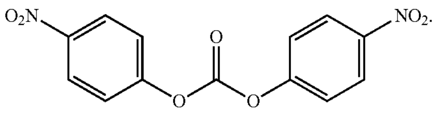 [SMILES: O=C(Oc1ccc([N+](=O)[O-])cc1)Oc1ccc([N+](=O)[O-])cc1]

2. The method according to claim 1, wherein solvent used in the condensation reaction is one or more selected from the group consisting of tetrahydrofuran, dioxane, acetonitrile, DMF, DMSO, water, methanol, ethanol, dichloromethane, chloroform, and carbon tetrachloride.

* * * * *